(12) United States Patent
Wanebo

(10) Patent No.: US 9,968,570 B2
(45) Date of Patent: May 15, 2018

(54) COMPOSITIONS AND METHODS FOR TREATING CANCER

(71) Applicant: Chemo-Enhanced LLC, Woonsocket, RI (US)

(72) Inventor: Harold J. Wanebo, Bristol, RI (US)

(73) Assignee: Chemo-Enhanced LLC, Woonsocket, RI (US)

( * ) Notice: Subject to any disclaimer, the term of this patent is extended or adjusted under 35 U.S.C. 154(b) by 0 days. days.

(21) Appl. No.: 14/760,510

(22) PCT Filed: Jan. 14, 2014

(86) PCT No.: PCT/US2014/011425
§ 371 (c)(1),
(2) Date: Jul. 13, 2015

(87) PCT Pub. No.: WO2014/110555
PCT Pub. Date: Jul. 17, 2014

(65) Prior Publication Data
US 2016/0051500 A1    Feb. 25, 2016

Related U.S. Application Data

(60) Provisional application No. 61/752,193, filed on Jan. 14, 2013, provisional application No. 61/788,281, filed on Mar. 15, 2013.

(51) Int. Cl.
| | | |
|---|---|---|
| *A61K 31/164* | (2006.01) | |
| *A61K 47/14* | (2017.01) | |
| *A61K 31/337* | (2006.01) | |
| *A61K 9/00* | (2006.01) | |
| *A61K 9/127* | (2006.01) | |
| *A61K 39/395* | (2006.01) | |
| *A61K 31/7068* | (2006.01) | |
| *A61K 33/24* | (2006.01) | |
| *C07K 16/28* | (2006.01) | |
| *A61K 31/282* | (2006.01) | |
| *A61K 31/513* | (2006.01) | |
| *A61K 47/24* | (2006.01) | |
| *A61K 39/00* | (2006.01) | |

(52) U.S. Cl.
CPC .......... *A61K 31/164* (2013.01); *A61K 9/0019* (2013.01); *A61K 9/1271* (2013.01); *A61K 31/282* (2013.01); *A61K 31/337* (2013.01); *A61K 31/513* (2013.01); *A61K 31/7068* (2013.01); *A61K 33/24* (2013.01); *A61K 39/395* (2013.01); *A61K 39/39558* (2013.01); *A61K 47/14* (2013.01); *A61K 47/24* (2013.01); *C07K 16/2863* (2013.01); *A61K 2039/505* (2013.01)

(58) Field of Classification Search
USPC .......... 424/133.1; 514/449, 49, 274
See application file for complete search history.

(56) References Cited

U.S. PATENT DOCUMENTS

| | | | |
|---|---|---|---|
| 7,015,251 B1 | 3/2006 | Wanebo et al. | |
| 7,820,718 B1 | 10/2010 | Wanebo et al. | |
| 8,216,607 B2 | 7/2012 | Wanebo | |
| 8,747,891 B2 | 6/2014 | Kester et al. | |
| 9,526,709 B2 | 12/2016 | Wanebo | |
| 2005/0249795 A1 | 11/2005 | Zhang et al. | |
| 2008/0033039 A1 | 2/2008 | Wanebo | |
| 2008/0058274 A1* | 3/2008 | Barenholz | A61K 9/1272 514/34 |
| 2008/0096840 A1 | 4/2008 | Kolesnick et al. | |
| 2009/0042810 A1 | 2/2009 | Chung | |
| 2009/0246271 A1 | 10/2009 | Wanebo | |
| 2009/0286847 A1 | 11/2009 | Fang et al. | |
| 2012/0282177 A1 | 11/2012 | Rohlff et al. | |

FOREIGN PATENT DOCUMENTS

| | | | | |
|---|---|---|---|---|
| WO | WO-2000/059517 A1 | 10/2000 | | |
| WO | WO-2007/143175 A2 | 12/2007 | | |
| WO | WO-2012/088414 A1 | 6/2012 | | |
| WO | WO 2012088414 A1 * | 6/2012 | ......... | A61K 39/0011 |

OTHER PUBLICATIONS

Lin et al. (2012) KRAS Mutation Is a Predictor of Oxaliplatin Sensitivity in Colon Cancer Cells. PLoS ONE 7(11): e50701.*
Bokemeyer et al. Annals of Oncology 22: 1535-1546, 2011.*
Abu Lila et al. Journal of Controlled Release 137 (2009) 8-14.*
Modrak, D. E. et al., "Synergistic Interaction between Sphingomyelin and Gemcitabine Potentiates Ceramide-Mediated Apoptosis in Pancreatic Cancer", *Cancer Research*, 64:8405-8410 (2004).
Perabo, F. G. E., et al., "Preclinical evaluation of gemcitabine/paclitaxel-interactions in human bladder cancer lines", *Anticancer Research*, 23:4805-4814 (2003) (Abstract).
Stover, T. C. et al., "Systemic Delivery of Liposomal Short-Chain Ceramide Limits Solid Tumor Growth in Murine Models of Breast Adenocarcinoma", *Clinical Cancer Res.*, 11(9):3465-3474 (May 1, 2005).
Tolis, C. et al., "Cell Cycle Disturbances and Apoptosis Induced by Topotecan and Gemcitabine on Human Lung Cancer Cell Lines", *European Journal of Cancer*, 35(5):796-807 (1999).
Trosko, J. E. et al., "Mechanism of up-regulated gap junctional intercellular communication during chemoprevention and chemotherapy of cancer", *Mutation Research*, 480-481:291-229 (2001).
Arlt et al., "Role of NF-κb and Akt/PI3K in the resistance of pancreatic carcinoma cell lines against gemcitabine-induced cell death," Oncogene, 22:3243-3251 (2003).
Garassino et al., "Different types of K-Ras mutations could affect drug sensitivity and tumour behaviour in non-small-cell lung cancer," Annals of Oncology, 22(1):235-237 (2011).

(Continued)

Primary Examiner — Jeffrey S Lundgren
Assistant Examiner — Michael J Schmitt
(74) Attorney, Agent, or Firm — Hathaway P. Russell, Esq.; Foley Hoag LLP

(57) ABSTRACT

The present invention provides, in part, compositions and methods for treating cancer using a combination of C6-ceramide and other anti-cancer agents in certain vesicles.

21 Claims, 16 Drawing Sheets

(56) References Cited

OTHER PUBLICATIONS

Guo et al., "The AMPK agonist AICAR inhibits the growth of EGFRvIII-expressing glioblastomas by inhibiting lipogenesis," PNAS, 106(31):12932-12937 (2009).
International Search Report dated Apr. 29, 2014, from PCT/US2014/011425.
International Search Report dated Sep. 21, 2012, from PCT/US12/32143.
Ji et al., "Exogenous cell-permeable C6 ceramide sensitizes multiple cancer cell lines to Doxorubicin-induced apoptosis by promoting AMPK activaction and mTORC1 inhibition," Oncogene, 29:6557-6568 (2010).
Liu et al., "Compartmentalized Production of Ceramide at the Cell Surface," The Journal of Biological Chemistry, 270 (45):27179-27185 (1995).
Mehta et al., "Combined cytotoxic action of paclitaxel and ceramide against the human Tu138 head and neck squamous carcinoma cell line," Cancer Chemother. Pharmacol., 46:85-92 (2000).
Myrick et al., "Paclitaxel-induced apoptosis in Jurkat, a leukemic T cell line, is enhanced by ceramide," Leukemia Research, 23:569-578 (1999).
Pollastri et al., "Synthesis, structure, and thermal properties of 1,2-dipalmitoylgalloylglycerol (DPGG), a novel self-adhering lipid," Chemistry and Physics of Lipids, 104:67-74 (2000).
Poplin et al., "Phase III, Randomized Study of Gemcitabine and Oxaliplatin Versus Gemcitabine (fixed-dose rate infusion) Compared With Gemcitabine (30-minute infusion) in Patients With Pancreatic Carcinoma E6201: A Trial of the Eastern Cooperative Oncology Group," Journal of Clinical Oncology, 27(23):3778-3785 (2009).
Qiu et al., "Paclitaxel and ceramide synergistically induce cell death with transient activation of EGFR and ERK pathway in pancreatic cancer cells," Oncology Reports, 16:907-913 (2006).
Ray et al., "Epithelial Tissues Have Varying Degrees of Susceptibility to $Kra^{G12D}$-Initiated Tumorigenesis in a Mouse Model," PLoS One, 6(2):e16786 (2011).
Roock et al., "Association of KRAS p. G13D Mutation With Outcome in Patients With Chemotherapy-Refractory Metastic Colorectal Cancer Treated with Cetuximab," JAMA, 304(16):1812-1820 (2010).
Roth et al., "Prognostic Role of KRAS and BRAF in Stage II and III Resected Colon Cancer: Results of the Translational Study on the PETACC-3, EORTC 40993, SAKK 60-00 Trial," Journal of Clinical Oncology, 28(3):466-474 (2010).
Shrayer et al., "Apoptosis signal ceramide c6 synergizes anti-tumor effects of paclitaxel oxaliplatin & cisplatin on growth of pancreatic cancer in SCID mice," Journal of Clinical Oncology, ASCO, 24(18S) (2006) Abstract 13135.
Shrayer et al., "Ceramide (C6) significantly augments the anti-tumor effect of paclitaxol on the engrafted L3.6 pancreatic CA," ASCO, 22:243 (2003) Abstract 972.
Stathopoulos et al., "Present Treatment and Future Expectations in Advanced Pancreatic Cancer," Anticancer Research, 28:1303-1308 (2008).
Stover et al., "Liposomal Delivery Enhances Short-Chain Ceramide-Induced Apoptosis of Breast Cancer Cells," Journal of Pharmacology and Experimental Therapeutics, 307(2):468-475 (2003).
Tettamanti et al., "Salvage pathways in glycosphingolipid metabolism," Biochimie, 85:423-437 (2003).
Van Vlerken et al., "Augmentation of Therapeutic Efficacy in Drug-Resistant Tumor Models Using Ceramide Coadministration in Temporal-Controlled Polymer-Blend Nanoparticle Delivery Systems," The AAPS Journal, 12(2):171-180 (2010).
Wanebo et al., "Abstract 4767: C6 ceramide sensitizes multiple aggressive pancreatic cancer cell lines to gemcitabine, paclitaxel and cetuximab mediated anti tumor effects in vivo and in vitro," Cancer Research, 71(8):4767 Abstract.
Wanebo et al., "The apoptosis signal ceramide (C6) significantly enhances the anti-tumor effects of a variety of chemo therapeutic drug classes D," Ann. Surg. Oncol., 15(S2):69 (2008) Abstract P116.
Zhu et al., "C6-ceramide synergistically potentiates the anti-tumor effects of histone deacetylase inhibitors via AKT dephosphorylation and α-tublin hyperacetylation both in vitro and in vivo," Cell Death and Disease, 2:(e117):1-12 (2011).
Zolnik et al., "Rapid Distribution of Liposomal Short-Chain Ceramide in Vitro and in Vivo," Drug Metabolism and Disposition, 36(8):1709-1715 (2008).
Beiner et al. "Ras Antagonist Inhibits Grwoth and Chemosensitizes Human Epithelial Ovarian Cancer Cells," Int. Gynecol. Cancer, 16(Suppl. 1): 200-206 (2006).
Voskoglou-Nomolkos, "Clinical Predictive Value of the in Vitro Cell Line, Human Xenograft, and Mouse Allograft Preclinical Cancer Models," Clinical Cancer Research,9: 4227-4239 (2003).
Zhang et al., "Kinase suppressor of Ras is ceramide-activated protein kinase," Cell, 89(1): 63-72 (1997).
Zundelevich et al., "Suppression of Lung Cancer Tumor Growth in a Nude Mouse Model by the Ras Inhibitor Salirasib (farnesylthiosalicyclic acid)," Mol. Cancer Ther. 6(6): 765-1773 (Jun. 2007).

* cited by examiner

| | No Chemo | Taxol | Gemcitabine | Certuximab |
|---|---|---|---|---|
| Ctrl | 100% | 87% | 70% | 90% |
| 5:89:6 DPGG:DOPC:C6Ceramide (5#) | 90% | 42% | 40% | 33% |
| 5:89:6 DPGG:DOPC:PBS (6#) | 108% | 76% | 36% | 77% |

Taxol: 0.1 µ g/ml   Gemcitambine: 5 µ g/ml   Certuximab: 25 µ g/ml
5#-5:89:6 DPGG:DOPC:C6Ceramide 1 µ g/ml
6#-5:89:6 DPGG:DOPC:PBS 1 µ g/ml No.
5    5:89:6  DPGG:DOPC:C6Ceramide
6    5:89:6  DPGG:DOPC: PBS Ctrl
7    5:95  180  PEG2PE:DOPC C6Ceramide
8    5:95  180  PEG2PE:DOPC PBS Ctrl
         C6Ceramide: 10 μg/ml

COMPOSITIONS AND METHODS FOR TREATING CANCER

RELATED APPLICATIONS

This application is a 35 U.S.C. § 371 U.S. national entry of International Application PCT/US2014/011425 having an international filing date of Jan. 14, 2014, which claims the benefit of priority to U.S. Provisional Patent Application Ser. No. 61/752,193, filed Jan. 14, 2013, and 61/788,281, filed Mar. 15, 2013; the contents of which are hereby incorporated by reference.

SEQUENCE LISTING

The instant application contains a Sequence Listing which has been submitted electronically in ASCII format and is hereby incorporated by reference in its entirety. Said ASCII copy, created on Oct. 19, 2015, is named WAR-002.01_SL.txt and is 5,378 bytes in size.

BACKGROUND OF THE INVENTION

Membrane Sphingolipids and Cancer Therapeutics

Membrane sphingolipids have been shown to be biologically active and exert numerous regulatory effects on cellular functions including modulating cell growth and differentiation. Ceramides, found in high concentrations within the cell membrane, are a family of lipid molecules composed of sphingosine and a fatty acid which function as structural elements, as well as signaling molecules. Studies have demonstrated important relationships between ceramide production and apoptosis in tumor cells and suggest that processes which enhance intracellular ceramide accumulation may provide in favorable proapoptotic effects during cancer chemotherapy. Cell permeable short chain ceramides (C2- or C6-ceramide) have shown activity relevant to therapeutically treating cancer indications. For example, such ceramide forms have an anti-cancer effect on many cancer cell lines, including melanoma and soft tissue sarcoma, Jurkat leukemia, and head and neck squamous cancer cell lines. Ceramides C2, C6 and their analogues have also been shown to induce cell cycle arrest in a variety of tumor types. Generation of endogenous ceramide has been shown to mediate apoptosis induced by a variety of anti-cancer drugs including daunorubicin, doxorubicin, ara-C, suramin, and paclitaxel (i.e., Taxol). Despite these observations, however, the molecular mechanisms underlying the therapeutically beneficial effects of ceramide, particularly cell permeable ceramides such as C6-ceramide, are unknown. This lack of understanding has hindered the development of compositions and methods containing ceramide (e.g., C6-ceramide) in combination with other agents that enhance the specific anti-cancer pathways affected by ceramide and/or overcome the pro-survival side effects of many anti-cancer therapeutics currently used in the clinic.

Vesicles

Large particulate assemblies of biologically compatible materials, such as liposomes, have been used as carriers for administration of drugs and paramagnetic contrast agents. U.S. Pat. Nos. 5,077,057 and 5,277,914 teach preparation of liposome or lipidic particle suspensions having particles of a defined size, particularly lipids soluble in an aprotic solvent, for delivery of drugs having poor aqueous solubility. U.S. Pat. No. 5,213,804 teaches liposome compositions containing an entrapped agent, such as a drug, which are composed of vesicle-forming lipids and 1 to 20 mole percent of a vesicle-forming lipid derivatized with hydrophilic biocompatible polymer and sized to control its biodistribution and recirculatory half life.

U.S. Pat. Nos. 5,512,294 and 6,090,408, and 6,132,764 describe the use of polymerized liposomes for various biological applications. The contents of these patents, and all others patents and publications referred to herein, are incorporated by reference herein in their entireties. One listed embodiment is to targeted polymerized liposomes which may be linked to or may encapsulate a therapeutic compound (e.g. proteins, hormones or drugs), for directed delivery of a treatment agent to specific biological locations for localized treatment. Other publications describing liposomal compositions include U.S. Pat. Nos. 5,663,387, 5,494,803, and 5,466,467.

In order to provide a therapeutic effect, a sufficient concentration of an active agent must be delivered to a targeted site. So, there is a need for recirculation of the active agent in the body. Active agents and delivery systems that avoid rapid endocytosis by the reticuloendothelial (RE) system or rapid filtration by the kidney are desirable. Experience with magnetic resonance contrast agents has provided useful information regarding circulation lifetimes. Small molecules, such as gadolinium diethylenetriaminepentaacetic acid, tend to have limited circulation times due to rapid renal excretion while most liposomes, having diameters greater than 800 nm, are quickly cleared by the reticuloendothelial system. Attempts to solve these problems have involved use of macromolecular materials, such as gadolinium diethylenetriaminepentaacetic acid-derived polysaccharides, polypeptides, and proteins. These agents have not achieved the versatility in chemical modification to provide for both long recirculation times and active targeting.

Accordingly, there is a great need in the art to provide anti-cancer therapeutics and delivery systems.

SUMMARY OF THE INVENTION

The present invention relates to vesicles for delivery of ceramide (e.g., C6-ceramide), in combination with one or more anti-cancer agents, e.g., a chemotherapeutic agent, for the treatment of cancer. The present invention also relates to compositions and methods for treating certain cancers (e.g., cancers characterized by hyperactive KRAS mutant polypeptides and/or pancreatic or colorectal cancer), wherein cancer cells are contacted with an effective amount of a vesicle comprising ceramide (e.g., C6-ceramide) and an effective amount of at least one (i.e., one or more) anti-cancer agents (e.g., a chemotherapeutic agent, an enhancer of the AMPK signaling pathway, an inhibitor of the PI3K/AKT/mTORC1 signaling pathway, an inhibitor of the MEK/ERK signaling pathway, and combinations thereof).

In one embodiment, the invention provides a method for treating cancer comprising the step of: contacting a cancer cell with an effective amount of a composition comprising (a) C6-ceramide; (b) an anti-cancer agent; and (c) a lipid, wherein the lipid comprises 1,2-dipalmitoyl-sn-glycero-3-galloyl or 1,2-distearoyl-sn-glycero-3-phosphoethanolamine-N-[methoxy(polyethylene glycol)-2000] to treat cancer.

In another aspect of the invention, the composition consists essentially of (a) C6-ceramide; (b) the anti-cancer agent; and (c) a lipid consisting essentially of 1,2-dipalmitoyl-sn-glycero-3-galloyl and 1,2-dioleoyl-sn-glycero-3-phosphocholine. In another aspect of the invention, the composition consists essentially of (a) C6-ceramide; (b) the anti-cancer agent; and (c) a lipid consisting essentially of 1,2-dipalmitoyl-sn-glycero-3-galloyl (DPGG) and 1,2-dioleoyl-sn-glycero-3-phosphocholine (DOPC); and the ratio of C6-ceramide:DPGG:DOPC is about 6:5:89. In another aspect of the invention, the composition consists essentially of (a) C6-ceramide; (b) the anti-cancer agent; and (c) a lipid consisting essentially of 1,2-distearoyl-sn-glycero-3-phosphoethanolamine-N-[methoxy(polyethylene glycol)-2000] and 1,2-dioleoyl-sn-glycero-3-phosphocholine. In another aspect of the invention, the composition consists essentially of (a) C6-ceramide; (b) the anti-cancer agent; and (c) a lipid consisting essentially of 1,2-distearoyl-sn-glycero-3-phosphoethanolamine-N-[methoxy(polyethylene glycol)-2000] (18:0 PEG2 PE) and 1,2-dioleoyl-sn-glycero-3-phosphocholine (DOPC); and ratio of C6-ceramide:(18:0 PEG2 PE):DOPC is about 1:5:95.

In another aspect of the invention, the anti-cancer agent is selected from the group consisting of paclitaxel, gemcitabine, oxaliplatin, cisplatin, cetuximab, panitumumab, erlotinib, daunorubicin, doxorubicin, cytosine arabinoside, and suramin. In another aspect of the invention, the anti-cancer agent is paclitaxel. In another aspect of the invention, the anti-cancer agent is gemcitabine. In another aspect of the invention, the anti-cancer agent is cetuximab.

In another aspect of the invention, the treatment of cancer is determined by analyzing at least one condition caused by contacting the cell with the composition relative to the state of the condition in the absence of contacting the cell with the composition, wherein the at least one condition is selected from the group consisting of increased apoptosis, decreased mean rate of tumor development (MRTD), decreased mean tumor volume (MTV), decreasing mean tumor size (MTS), increasing mean body weight (MBW), increased mean survival time (MST), increased survival until mortality, pathological complete response, clinical complete remission, clinical partial remission, clinical stable disease, recurrence-free survival, metastasis free survival, and disease free survival.

In another aspect of the invention, the condition is affected synergistically with respect to contacting the cell with the composition relative to the condition affected by contacting the cell with (a) alone, (b) alone, (c) alone, (a) and (b) together, (a) and (c) together, or (b) and (c) together.

BRIEF DESCRIPTION OF THE FIGURES

FIG. 7A and FIG. 7D: SCID/Beige/Taconic nude male mice, 22-25 g, 6-8 weeks old were ear tagged and randomized into 4 different groups (Control, Ceramide, Gemcitabine, Ceramide+Gemcitabine) combining 5 mice each prior to inoculation s.c. with 2×10$^6$ L3.6 cells in a volume 0.1 ml into the internal surface of the right thigh. Treatment was started 4 days after L3.6 cell injection with thrice weekly (3×/wk) intraperitoneal (I.P.) injections of Gemcitabine (two doses: 5.0 and 10.0 mg/ml) with or without C6-Ceramide (10 mg/ml) for 2 weeks. Combination of Gemcitabine (5 or 10 mg/kg) and Ceramide (10 mg/kg) was associated with reduced tumor growth (FIG. 7C, 7D) and increased survival at both dose levels of Gemcitabine. Mice survival (A, B and E) and tumor volume (in cm$^3$) (C and D) were recorded (E). In (E), the left bar indicates treatment without C6, and the right bar indicates treatment with C6.

In FIG. 9, left panel, the DMSO=left bar; LY294002=second left bar; U0126=middle bar; Rapamycin=second right bar; and LY+U0126=right bar.

DETAILED DESCRIPTION OF THE INVENTION

Overview

Figure 1:
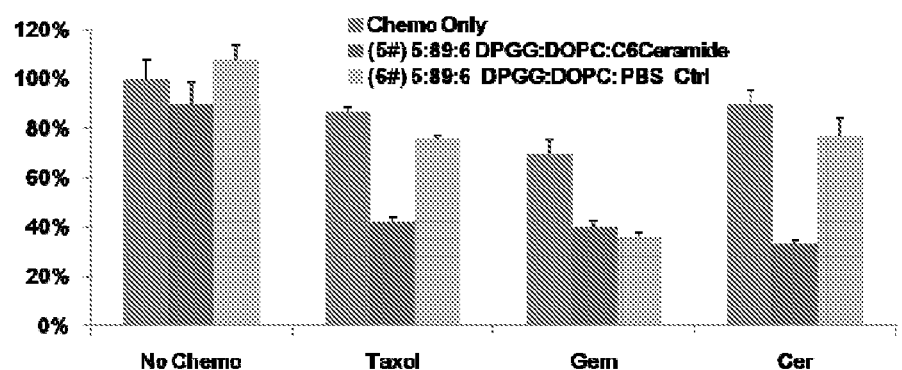
FIG. 1 depicts the sensitivity of L3.6 cells to three active agents as modified by the lipid vesicles formulated from DPGG:DOPC:C6-Ceramide compared to DPGG:DOPC PBS. Percentage cell survival is shown for cells treated with vesicles and no active agent (No chemo), Paclitaxel (Taxol), gemcitabine (Gem), or cetuximab (Cer). Cell viability is noticeably reduced in the presence of an active agent with lipid vesicles that include DPGG, DOPC, and C6-Ceramide. Left bar=chemo only; middle bar=#5; right bar=#6.

The present invention relates to vesicles for delivery of ceramide (e.g., C6-ceramide), in combination with one or more anti-cancer agents, e.g., a chemotherapeutic agent, for the treatment of cancer. The present invention also relates to compositions and methods for treating certain cancers (e.g., cancers characterized by hyperactive KRAS mutant polypeptides and/or pancreatic or colorectal cancer), wherein cancer cells are contacted with an effective amount of a vesicle comprising ceramide (e.g., C6-ceramide) and an effective amount of at least one (i.e., one or more) anti-cancer agents (e.g., a chemotherapeutic agent, an enhancer of the AMPK signaling pathway, an inhibitor of the PI3K/AKT/mTORC1 signaling pathway, an inhibitor of the MEK/ERK signaling pathway, and combinations thereof).

In one embodiment, the invention provides a method for treating cancer comprising the step of: contacting a cancer cell with an effective amount of a composition comprising (a) C6-ceramide; (b) an anti-cancer agent; and (c) a lipid, wherein the lipid comprises 1,2-dipalmitoyl-sn-glycero-3-galloyl or 1,2-distearoyl-sn-glycero-3-phosphoethanolamine-N-[methoxy(polyethylene glycol)-2000] to treat cancer.

In one aspect of the invention, the cell is present in an in vitro sample, an ex vivo sample, or a subject in vivo. In another aspect of the invention, the cell is present in a subject in vivo; and the subject is a mammal. In certain embodiments, the subject is a human. In another aspect of the invention, the cell is comprised within a tumor.

In yet another aspect of the invention, the cancer is selected from the group consisting of pancreatic cancer, colorectal cancer, breast cancer, ovarian cancer, transitional cell bladder cancer, melanoma, basal cell carcinoma, glioblastoma multiforme, endometrial cancer, cervical cancer, osteosarcoma, bronchogenic lung cancer, thyroid cancer, prostate cancer, uterine cancer, testicular cancer, gastric cancer, soft tissue and osteogenic sarcomas, neuroblastoma, Wilms' tumor, malignant lymphoma, acute myeloblastic leukemia, acute lymphoblastic leukemia, Kaposi's sarcoma, Ewing's tumor, refractory multiple myeloma, and squamous cell carcinomas of the head, neck, cervix, and vagina. In another aspect of the invention, the cancer is pancreatic cancer. In another aspect of the invention, the cancer is pancreatic adenocarcinoma.

In certain embodiments, the cancer cell has an activating KRAS mutation. In another aspect of the invention, the activating KRAS mutations is a human KRAS polypeptide having a mutation selected from the group consisting of G12C, G12A, G12D, G12R, G12S, G12V, G13C, and G13D.

In another aspect of the invention, the composition consists essentially of (a) C6-ceramide; (b) the anti-cancer agent; and (c) a lipid consisting essentially of 1,2-dipalmitoyl-sn-glycero-3-galloyl and 1,2-dioleoyl-sn-glycero-3-phosphocholine. In another aspect of the invention, the composition consists essentially of (a) C6-ceramide; (b) the anti-cancer agent; and (c) a lipid consisting essentially of 1,2-dipalmitoyl-sn-glycero-3-galloyl (DPGG) and 1,2-dioleoyl-sn-glycero-3-phosphocholine (DOPC); and the ratio of C6-ceramide:DPGG:DOPC is about 6:5:89. In another aspect of the invention, the composition consists essentially of (a) C6-ceramide; (b) the anti-cancer agent; and (c) a lipid consisting essentially of 1,2-distearoyl-sn-glycero-3-phosphoethanolamine-N-[methoxy(polyethylene glycol)-2000] and 1,2-dioleoyl-sn-glycero-3-phosphocholine. In another aspect of the invention, the composition consists essentially of (a) C6-ceramide; (b) the anti-cancer agent; and (c) a lipid consisting essentially of 1,2-distearoyl-sn-glycero-3-phosphoethanolamine-N-[methoxy(polyethylene glycol)-2000] (18:0 PEG2 PE) and 1,2-dioleoyl-sn-glycero-3-phosphocholine (DOPC); and ratio of C6-ceramide:(18:0 PEG2 PE):DOPC is about 1:5:95.

In another aspect of the invention, the weight ratio of (a):(b) is from about 2:1 to about 1:40. In another aspect of the invention, the weight ratio of (a):(b) is about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, or about 1:25. In another aspect of the invention, the weight ratio of (a):(b) is about 1:1, about 1:5, or about 1:25.

In another aspect of the invention, the cell is present in a subject in vivo; and the cell is contacted with the composition by an administration route selected from the group consisting of intravenous, intraperitoneal, intrathecal, intralymphatic, intramuscular, intralesional, parenteral, epidural, subcutaneous, pleural, topical, oral, nasal, anal, ocular and otic.

In another aspect of the invention, the anti-cancer agent is selected from the group consisting of paclitaxel, gemcitabine, oxaliplatin, cisplatin, cetuximab, panitumumab, erlotinib, daunorubicin, doxorubicin, cytosine arabinoside, and suramin. In another aspect of the invention, the anti-cancer agent is paclitaxel. In another aspect of the invention, the anti-cancer agent is gemcitabine. In another aspect of the invention, the anti-cancer agent is cetuximab.

In another aspect of the invention, the treatment of cancer is determined by analyzing at least one condition caused by contacting the cell with the composition relative to the state of the condition in the absence of contacting the cell with the composition, wherein the at least one condition is selected from the group consisting of increased apoptosis, decreased mean rate of tumor development (MRTD), decreased mean tumor volume (MTV), decreasing mean tumor size (MTS), increasing mean body weight (MBW), increased mean survival time (MST), increased survival until mortality, pathological complete response, clinical complete remission, clinical partial remission, clinical stable disease, recurrence-free survival, metastasis free survival, and disease free survival.

In another aspect of the invention, the condition is affected synergistically with respect to contacting the cell with the composition relative to the condition affected by contacting the cell with (a) alone, (b) alone, (c) alone, (a) and (b) together, (a) and (c) together, or (b) and (c) together.

In order that the present invention may be more readily understood, certain terms are first defined. Additional definitions are set forth throughout the detailed description. Published PCT application WO12/138739 is hereby incorporated by reference in its entirety.

I. Definitions

The articles "a" and "an" are used herein to refer to one or to more than one (i.e. to at least one) of the grammatical object of the article. By way of example, "an element" means one element or more than one element.

As used herein, the term "activating KRAS mutation" refers to a mutation in a KRAS polypeptide that causes enhanced KRAS activity relative to the control wild-type KRAS polypeptide without the mutation. In one embodiment, the activating KRAS mutation is selected from the group consisting of G12C; G12A; G12D; G12R; G12S; G12V; G13C; G13D of the human KRAS polypeptide. The term "altered activity" refers to an activity of a molecule (e.g., a polypeptide) which is increased or decreased in a defined state (e.g., in a mutated or diseased state and/or sample), as compared to the activity of the biomarker in a control state (e.g., in a wild type or normal, control state and/or sample). Altered activity may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors, or altered methylation status. Such altered activity can be at least 10%, 20%, 30%, 40%, 50%, 60%, 70%, 80%, 90%, 100%, 150%, 200%, 250%, 300%, 350%, 400%, 450%, 500%, 1000%, or more modulated (e.g., upregulated or downregulated).

As used herein, the term "anti-cancer response" to therapy relates to any response of the cancer to therapy, preferably to a change in tumor mass and/or volume after initiation of neoadjuvant or adjuvant chemotherapy. Hyperproliferative disorder response may be assessed in a neoadjuvant or adjuvant situation where the size of a tumor after systemic intervention can be compared to the initial size and dimensions as measured by CT, PET, mammogram, ultrasound or palpation. Response may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy.

As used herein, the term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

As used herein, the term "cancer" is intended to encompass a tumor, including both in vitro and in vivo tumors that form in any organ or body part of the subject. Examples of the types of tumors intended to be encompassed by the present invention include those tumors associated with breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys. Specifically, the tumors whose growth rate is inhibited by the present invention include basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

In one embodiment, the cancer is pancreatic cancer. The term "pancreatic cancer" as used herein, includes adenomas, adenocarcinomas, gastrinomas, somatostatinomas, insulinomas and glucagonomas of the pancreas. As used herein, the term "adenocarcinoma" is carcinoma that develops in the lining or inner surface of an organ and is derived from glandular tissue or in which the tumor cells form recognizable glandular structures. As used interchangeably herein, the terms, "pancreatic adenocarcinoma," or "pancreatic ductal adenocarcinoma" is an adenocarcinoma of the pancreas. In one embodiment, pancreatic adenocarcinomas arise from the progression of lesions that occur in the pancreatic ducts (pancreatic intraepithelial neoplasia, referred to herein as "PanIN"). Pancreatic cancer is a malignant growth of the pancreas that mainly occurs in the cells of the pancreatic ducts. This disease is the ninth most common form of cancer, yet it is the fourth and fifth leading cause of cancer deaths in men and women, respectively. Cancer of the pancreas is almost always fatal, with a five-year survival rate that is less than 3%. The most common symptoms of pancreatic cancer include jaundice, abdominal pain, and weight loss, which, together with other presenting factors, are nonspecific in nature. Thus, diagnosing pancreatic cancer at an early stage of tumor growth is often difficult and requires extensive diagnostic work-up, often times including exploratory surgery. Endoscopic ultrasonography and computed tomography are the best noninvasive means available today for diagnosis of pancreatic cancer. However, reliable detection of small tumors, as well as differentiation of pancreatic cancer from focal pancreatitis, is difficult. The vast majority of patients with pancreatic cancer are presently diagnosed at a late stage when the tumor has already extended outside of the capsule to invade surrounding organs and/or has metastasized extensively (Gold et al. (2001) *Crit. Rev. Oncology/Hematology*, 39:147-54). Late detection of the disease is common, and early pancreatic cancer diagnosis is rare in the clinical setting. This is significant, since late detection of pancreatic cancer results in low survival rate. Current treatment procedures available for pancreatic cancer have not led to a cure, or to a substantially improved survival time. Surgical resection has been the only modality that offers a chance at survival. However, due to a large tumor burden, only 10% to 25% of patients are candidates for "curative resection." For those patients undergoing a surgical treatment, the five-year survival rate is still poor, averaging only about 10%. A "non-endocrine pancreatic cancer" generally refers to cancers arising from the exocrine pancreatic glands. The term excludes pancreatic insulinomas and includes pancreatic carcinoma, pancreatic adenocarcinoma, adenosquamous carcinoma, squamous cell carcinoma and giant cell carcinoma and precursor lesions such as pancreatic intra-epithelial neoplasia (PanIN), mucinous cyst neoplasms (MCN) and intrapancreatic mucinous neoplasms (IPMN), which are neoplastic but not yet malignant. The terms "pancreatic cancer" and "non-endocrine pancreatic cancer" are used interchangeably herein.

In another embodiment, the cancer is colorectal cancer. Colon cancer is located in the large intestine, while rectal cancer is in the rectum. The difference between these two cancers is the location in the large intestine where the cancer occurs. Therefore, the term colorectal cancer is often used to refer to cancer in both locations. Colorectal cancer is third most common leading causes of cancer death in the United States. According to the "American Cancer Society Colorectal Cancer Facts and Figures. 2011-2013" (Atlanta, American Cancer Society, 2011), in 2001, the incidence rates of colorectal cancer per 100,000 are about 57.2 among male, and about 42.5 among female. In comparison, the mortality rates are 21.2 among male, and 14.9 among female per 100,000. As a whole, there will be about 141,000 new cases and 49,000 deaths in 2011. The common stages of colorectal cancer includes: Stage 0: when cancer is only on the innermost layer of the intestine; Stage I: when cancer is in the inner layer of the colon; Stage II: when cancer has spread through the muscle wall of the colon; Stage III: when cancer has spread to the lymph nodes; and Stage 1V: when cancer has spread to other organs. The most effective approach to treat colorectal cancer is early detection before symptoms develop by undergoing periodic colonoscopy or sigmoidoscopy when a person is 50 years or older, or has either a family history or personal history of colon cancer. The treatment options of colorectal cancer are surgery, radiation therapy and chemotherapy. 5-Fluorouracil, oxaliplatin and irinoteccan are commonly used chemotherapeutic agents for colorectal cancer. About 30% of metastatic colorectal cancer (CRC) include KRAS mutation. KRAS mutant CRC is highly resistant to multi drug therapy, e.g., FOLFOX chemo therapy plus anti EGFR Cetuximab, as compared to chemo response in KRAS wild-type cancer. The chemo response to FOLFOX in wild type CRC is approximately 60% (FOL-FOX & Cetuximab) vs. 30-40% with FOLFOX alone. In contrast, in KRAS mutant cancer, the response to FOLFOX is around 30% and it is not enhanced by Cetuximab because of the inhibiting effect of KRAS mutant CRC on the anti EGFR activity of Cetuximab.

As used herein, the term "cancer cell" is intended to include tumor cells, and refers to cells that divide at an abnormal (increased) rate. Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; leukemias and lymphomas such as granulocytic leukemia, monocytic leukemia, lymphocytic leukemia, malignant lymphoma, plasmocytoma, reticulum cell sarcoma, or Hodgkin's disease; and tumors of the nervous system including glioma, meningioma, medulloblastoma, schwannoma or epidymoma.

As used herein "contacting cancer cells" is defined as exposing the cancer cells to one or more combinations of agents described herein. In one embodiment, such combinations can be administered to cancer cells, directly or indirectly, using local, regional or systemic means.

As used herein "decreasing the size of a tumor" is defined as a reduction in the size of a tumor. Such an effect can be accomplished by reducing the number of proliferating tumor cells in the tumor (e.g., by reducing cell division of the tumor cells) and/or by inducing cytotoxicity or cell death (apoptosis) of existing tumor cells. Accordingly, tumor growth is arrested or prevented.

As used herein, the term "EGFR inhibitor" refers to an inhibitor of the epidermal growth factor receptor (EGFR). In one embodiment, the EGFR inhibitor is an antibody such as Erbitux™ (cetuximab, Imclone Systems Inc.) and ABX-EGF (panitumumab, Abgenix, Inc.). In another embodiment the EGFR inhibitor is a small molecule that competes with ATP such as Tarceva™ (erlotinib, OSI Pharmaceuticals), Iressa™ (gefitinib, Astra-Zeneca), tyrphostins described by Dvir et al. (1991) JCB 113:857-865; tricyclic pyrimidine compounds disclosed in U.S. Pat. No. 5,679,683; compound 6-(2,6-dichlorophenyl)-2-(4-(2-diethylaininoethoxy)phenylamino)-8-methyl-8H-pyrido(2,3-d)pyrimidin-7-one (known as PD166285) disclosed in Panek et al. (1997) *J. Pharm. Exp. Therap.* 283:1433-1444).

As used herein "increasing apoptosis" is defined as an increase in the rate of programmed cell death, i.e. more cells are induced into the death process as compared to exposure (contact with) either gemcitabine alone or the ceramide alone. Increasing apoptosis also includes the inhibition of cell division which results in a decrease in the total number of viable cancer cells.

As used herein, the term "inhibiting cancer" or "inhibiting cancer cell growth" is intended to include the inhibition of undesirable or inappropriate cell growth. The inhibition is intended to include inhibition of proliferation including rapid proliferation. The term "inhibiting cancer cell growth" is also intended to encompass inhibiting tumor growth which includes the prevention of the growth of a tumor in a subject or a reduction in the growth of a pre-existing tumor in a subject. The inhibition also can be the inhibition of the metastasis of a tumor from one site to another. A cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "modulate" includes downregulation and upregulation. The term "downregulate," "decrease," "reduce," "inhibit," and the like are all used herein generally to mean a decrease by a statistically significant amount. The term "upregulate," "increase," "enhance," and the like are all used herein generally to mean an increase by a statistically significant amount. For example, an increase or a decrease can be by at least about 10%, 20%, 25%, 30%, 35%, 40%, 45%, 50%, 55%, 60%, 65%, 70%, 75%, 80%, 85%, 90%, 95%, 98%, 99%, 100%, 150%, 200%, 250%, 300%, 350%, 400%, 450%, 500%, 1000%, or more or any range in between 10-1000% inclusive as compared to a control. In some embodiments, the control can be a change in a cancer cell state such as cancer cell proliferation in the presence versus the absence of treatment. In another embodiment, the control can be activity of a wild type polypeptide of interest. An "overactivity" or "significantly higher level of activity" refers to an activity level of a molecule or test sample that is greater than the standard error of the assay employed to assess the activity, and is preferably at least twice, and more preferably three, four, five or ten or more times the activity relative to a reference or control sample and preferably, the average activity in several control samples. The term "underactivity" refers to the opposite of "overactivity."

A cancer cell is "resistant" to a therapeutic agent if its rate of growth is not inhibited, or inhibited to a very low degree, as a result of contact with the therapeutic agent when compared to its growth in the absence of contact with the therapeutic agent. The quality of being resistant to a therapeutic agent is a highly variable one, with different cancer cells exhibiting different levels of "resistance" to a given therapeutic agent under different conditions.

A cancer cell is "sensitive" to a therapeutic agent if its rate of growth is inhibited as a result of contact with a therapeutic agent, compared to its growth in the absence of contact with the therapeutic agent. The quality of being sensitive to a therapeutic agent is a variable one, with different cancer cells exhibiting different levels of "sensitivity" to a given therapeutic agent, under different conditions.

Determination of whether a patient is "sensitive" or "resistant" to a therapeutic agent and/or protocol can be readily made by the physician (the "attending clinician"), as one skilled in the art, by the use of known techniques. For example, a number of factors are considered by the attending clinician, including, but not limited to: the specific cancer involved; pharmacodynamic characteristics of the particular therapeutic agent; the size, age, and general health of the patient; the degree of or involvement or the severity of the cancer; the particular compound administered; the mode of administration; and other relevant circumstances.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

As used herein, the term "subject" shall mean any animal including, without limitation, a human, a mouse, a rat, a rabbit, a non-human primate, or any other mammal. In one embodiment, the subject is a primate. In another embodiment, the subject is a human.

As used herein, the term "synergistic" refers to a combination of therapeutic agents described herein, which, when taken together, is more effective than the additive effects of the individual therapies. A synergistic effect of a combination of therapies (e.g., a combination of therapeutic agents) permits the use of lower dosages of one or more of the therapeutic agent(s) and/or less frequent administration of the agent(s) to a subject with a disease or disorder, e.g., a proliferative disorder. The ability to utilize lower the dosage of one or more therapeutic agent and/or to administer the therapeutic agent less frequently reduces the toxicity associated with the administration of the agent to a subject without reducing the efficacy of the therapy in the treatment of a disease or disorder. In addition, a synergistic effect can result in improved efficacy of agents in the prevention, management or treatment of a disease or disorder, e.g. a proliferative disorder. Finally, a synergistic effect of a combination of therapies may avoid or reduce adverse or unwanted side effects associated with the use of either therapeutic agent alone. As used herein, the term "in combination" refers to the use of more than one therapeutic agent. The use of the term "in combination" does not restrict the order in which the therapeutic agents are administered to a subject with a disease or disorder, e.g., a proliferative disorder. A first therapeutic agent, such as a compound described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as an anti-cancer agent, to a subject with a disease or disorder, e.g. a proliferative disorder, such as cancer.

II. Therapeutic Agents and Pharmaceutical Compositions

The methods of the present invention use combinations of therapeutic agents in a pharmaceutical composition as described below.

A. Ceramide

The term "ceramide" generally refers to any N-acylsphingosine. Ceramides include sphingolipids in which the sphingosine is acylated with a fatty acid acyl CoA derivative to form an N-acylsphingosine. Ceramide may be either naturally occurring or chemically synthesized. Preferably, the carbon chain length is less than 18 carbons. Examples include C6-ceramide (N-hexanoyl-D-sphingosine), C2-ceramide (N-acetyl-D-sphingosine), C8-ceramide (N-octyl-D-sphingosine) and C16-ceramide (N-palmitoyl-D-sphingosine). Other ceramides are known to persons having ordinary skill in the art. In certain embodiments of the above-described methods and composition, the ceramide may be a C2-ceramide, C6-ceramide, C8-ceramide, C16-ceramide, or a higher order of ceramide. In one embodiment, the ceramide is C6-ceramide. For each embodiment of the present invention described herein relating to C6-ceramide, each of the other orders of ceramide known to the skilled artisan are also contemplated mutatis mutandis. Ceramide, which is normally lipid soluble, can be made water soluble according to well-known methods in order to enable contact with cancer cells (e.g., in a subject). Ceramide may be solubilized initially in alcohol and then subsequently diluted in saline or a cremophore.

The amount of ceramide used in in vitro studies is from about 5 µg/mL to-about 25 µg/mL. In animal studies evaluating the effect of C6-Ceramide in combination therapy of heterotransplanted human tumors in SCID mice, the ceramide dose levels are in the range of 5 to >10 mg/kg.

For each embodiment described herein, the amount of ceramide to other therapeutic agent described herein can be about paclitaxel 3.5-5.0 mg/kg, oxaliplatin 25 mg/kg, gemcitabine 10-20 mg/kg and cetuximab 6 mg/kg or greater or any range in between.

B. Therapeutic Agents

As used herein, the terms "anti-cancer agent" and "therapeutic agent" and "active agent" are defined broadly as anything that cancer cells, including tumor cells, may be exposed to in a therapeutic protocol for the purpose of inhibiting their growth or kill the cells. In one embodiments, such agents can be used according to the methods described herein either in conjunction with ceramide (e.g., C6-ceramide), in conjunction with each other (e.g., LY294002 plus gemcitabine, taxol plus U0126, taxol plus gemcitabine, etc.), or in any combination thereof. In the context of the present invention, such agents include, but are not limited to, chemotherapeutic agents, such as anti-metabolic agents, e.g., Ara AC, 5-FU and methotrexate, antimitotic agents, e.g., TAXOL, inblastine and vincristine, alkylating agents, e.g., melphalan, BCNU and nitrogen mustard, topoisomerase II inhibitors, e.g., VW-26, topotecan and Bleomycin, strand-breaking agents, e.g., doxorubicin and DHAD, cross-linking agents, e.g., cisplatin and CBDCA, radiation and ultraviolet light.

As used herein, the term "chemotherapeutic agent" is intended to include chemical reagents which inhibit the growth of proliferating cells or tissues wherein the growth of such cells or tissues is undesirable. Particular chemotherapeutic agents include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (vi) topoisomerase I poisons, such as camptothecin or topotecan; (vii)

topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) enhancers of the AMPK signaling pathway, (xi) inhibitors of the PI3K/AKT/mTORC1 signaling pathway, (xii) inhibitors of the MEK/ERK signaling pathway, (xiii) miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof (xiv) hormones such as glucocorticoids or fenretinide; and (xv) hormone antagonists, such as tamoxifen, finasteride or LHRH antagonists. In an embodiment, the chemotherapeutic compound is one or more of gemcitabine, cisplatin, doxorubicin, daunarubicin, paclitaxel, taxotere and mitomycin C. In a particular embodiment, the chemotherapeutic compound is one or more of gemcitabine, cisplatin and paclitaxel.

Chemotherapeutic agents are well known in the art (see e.g., Gilman A. G., et al., The Pharmacological Basis of Therapeutics, 8th Ed., Sec 12:1202-1263 (1990)), and are typically used to treat neoplastic diseases. The chemotherapeutic agents generally employed in chemotherapy treatments are listed below in Table 1.

TABLE 1

| CLASS | TYPE OF AGENT | NONPROPRIETARY NAMES (OTHER NAMES) |
|---|---|---|
| Alkylating | Nitrogen Mustards | Mechlorethamine ($HN_2$) |
| | | Cyclophosphamide |
| | | Ifosfamide |
| | | Melphalan (L-sarcolysin) |
| | | Chlorambucil |
| | Ethylenimines And Methylmelamines | Hexamethylmelamine Thiotepa |
| | Alkyl Sulfonates | Busulfan |
| Alkylating | Nitrosoureas | Carmustine (BCNU) |
| | | Lomustine (CCNU) |
| | | Semustine (methyl-CCNU) |
| | | Streptozocin (streptozotocin) |
| | Triazenes | Decarbazine (DTIC; imethyltriazenoimidazolecarboxamide) |
| | Alkylator | cis-diamminedichloroplatinum II (CDDP) |
| Antimetabolites | Folic Acid Analogs | Methotrexate (amethopterin) |
| | Pyrimidine Analogs | Fluorouracil ('5-fluorouracil; 5-FU) |
| | | Floxuridine (fluorode-oxyuridine; FUdR) |
| | | Cytarabine (cytosine arabinoside) |
| | | gemcitabine (deoxycytidine analog) |
| | Purine Analogs and Related Inhibitors | Mercaptopuine (6-mercaptopurine; 6-MP) |
| | | Thioguanine (6-thioguanine; TG) |
| | | Pentostatin (2'-deoxycoformycin) |
| | Vinca Alkaloids | Vinblastin (VLB) |
| | | Vincristine |
| | Topoisomerase Inhibitors | Etoposide |
| | | Teniposide |
| | | Camptothecin |
| | | Topotecan |
| | | 9-amino-campotothecin CPT-11 |
| Natural Products | Antibiotics | Dactinomycin (actinomycin D) |
| | | Adriamycin (Doxorubicin) |
| | | Daunorubicin (daunomycin; rubindomycin) |
| | | Doxorubicin |
| | | Bleomycin |
| | | Plicamycin (mithramycin) |
| | | Mitomycin (mitomycin C) |
| | | TAXOL (paclitaxel) |
| | | Taxotere |
| | Enzymes | L-Asparaginase |
| | Biological Response Modifiers | Interfon alfa interleukin 2 |
| Misc. Agents | Platinum Coordination Complexes | cis-diamminedichloroplatinum II (CDDP) |
| | | Carboplatin |
| | | Oxaliplatin |
| | | Cisplatin |
| | Anthracendione | Mitoxantrone |
| | Substituted Urea | Hydroxyurea |
| | Methyl Hydraxzine Derivative | Procarbazine (N-methylhydrazine, (MIH) |
| | Adrenocortical Suppressant | Mitotane (o,p'-DDD) Aminoglutethimide |

TABLE 1-continued

| CLASS | TYPE OF AGENT | NONPROPRIETARY NAMES (OTHER NAMES) |
|---|---|---|
| Hormones and Antagonists | Adrenocorticosteroids | Prednisone |
| | | Dexamethasone |
| | Progestins | Hydroxyprogesterone Caproate |
| | | Medroxyprogesterone Acetate |
| | | Megestrol acetate |
| | Estrogens | Diethylstilbestrol |
| | | Ethinyl estradiol |
| | Antiestrogen | Tamoxifen |
| | Androgens | Testosterone propionate |
| | | Fluoxymesterone |
| | Antiandrogen | Flutamide |
| | Gonadotropin-releasing Hormone analog | Leuprolide |

The chemotherapeutic agents used in the present methods can be a single agent or a combination of agents. Preferred combinations will include agents that have different mechanisms of action, e.g., the use of an anti-mitotic agent in combination with an alkylating agent.

As used herein, the term "pro-survival" or "pro-growth" pathways refer to signaling pathways used by cancer cells to promote their growth and/or survival. The term "pathway" is intended to mean a set of system components involved in two or more sequential molecular interactions that result in the production of a product or activity. A pathway can produce a variety of products or activities that can include, for example, intermolecular interactions, changes in expression of a nucleic acid or polypeptide, the formation or dissociation of a complex between two or more molecules, accumulation or destruction of a metabolic product, activation or deactivation of an enzyme or binding activity. Thus, the term "pathway" includes a variety of pathway types, such as, for example, a biochemical pathway, a gene expression pathway, and a regulatory pathway. Similarly, a pathway can include a combination of these exemplary pathway types. Intracellular signaling via several pathways, such as AMPK, PI3K/AKT, MEK/ERK, and JAK/STAT signaling pathways, leading to the activation of anti-apoptotic proteins and the inactivation of pro-apoptotic proteins (reviewed in Henson and Gibson, 2006, Cellular Signaling 18:2089-2097).

Without being bound by theory, it is believed that ceramide increases apoptosis in cancer cells and such desired cancer cell death is antagonized by pro-survival pathways. Accordingly, therapeutic agents that inhibit such pro-survival pathways are contemplated as useful therapeutic agents in combination with ceramide.

In one embodiment, the pro-survival pathway is the AMP-activated protein kinase (AMPK) signaling pathway. AMPK has a role in regulating the mTOR pathway. Mammalian target of rapamycin (mTOR) is a serine/threonine kinase and a key regulator of protein synthesis. To inhibit cell growth and protect cells from apoptosis induced by glucose starvation, AMPK phosphorylates TSC2 at Thr-1227 and Ser-1345 increasing the activity of the TSC1 and TSC-2 complex to inhibit m-TOR. In addition, AMPK inhibits mTOR action by phosphorylation on Thr-2446. Thus, AMPK indirectly and directly inhibits the activity of mTOR to limit protein synthesis. AMPK may also be a therapeutic target for many cancers that have constitutive activation of the PI3K-Akt signaling pathway. Treatment of various cancer cell lines by AICAR attenuated the cell proliferation both in-vitro and in-vivo studies (Rattan et al., JBC 280, 39582 (2005)). Reports link the treatment of metformin with a lower risk of cancer in diabetic patients (Evans et al., BMJ 330, 1304 (2005)). The activation of AMPK by AICAR has been shown to reduce expression of the lipogenic enzymes FAS and ACC, resulting in suppression of proliferation in prostate cancer cells. Many cancer cells display a markedly increased rate of de novo fatty acid synthesis correlated with high levels of FAS. Inhibition of FAS suppresses cancer cell proliferation and induces cell death. Thus, AMPK activation and inhibition of FAS activity is a clear target for pharmacological therapy of cancers.

In another embodiment, the pro-survival pathway is the PI3K/AKT/mTORC1 signaling pathway. The "PI3K/AKT signaling pathway" or "AKT signaling pathway" refers to one of the intracellular signaling pathways activated by the binding of growth factors to receptor tyrosine kinases. On activation, PI3K phosphorylates phosphatidylinositol-4,5-bisphosphate (PIP2) to phsophatidylinositol-3,4,5-triphosphate (PIP3), a process that is reversed by PTEN. PIP3 signals activate the kinase PDK1, which in turn activates the kinase AKT. The AKT protein family, which members are also called protein kinases B (PKB) plays an important role in mammalian cellular signaling. Akt kinase is a serine/threonine kinase which is a downstream effector molecule of phosphoinositide 3-kinase and is involved in protecting a cell from apoptosis. Akt kinase is thought to be involved in the progression of cancer because it stimulates cell proliferation and suppresses apoptosis. Akt1 is involved in cellular survival pathways, by inhibiting apoptotic processes. Akt1 is also able to induce protein synthesis pathways, and is therefore a key signaling protein in the cellular pathways that lead to skeletal muscle hypertrophy, and general tissue growth. Since it can block apoptosis, and thereby promote cell survival, Akt1 has been implicated as a major factor in many types of cancer. Akt is known to play a role in the cell cycle. Under various circumstances, activation of Akt was shown to overcome cell cycle arrest in G1 and G2 phases. Moreover, activated Akt may enable proliferation and survival of cells that have sustained a potentially mutagenic impact and, therefore, may contribute to acquisition of mutations in other genes. AKT (activation, amplification) and PTEN (mutation, deletion, epigenetic inactivation) are deregulated in many human cancers (Altomare et al., 2003, J. Cell Biochem. 88:470-476; Ruggeri et al., 1998, Mol. Carcinog. 21:81-86; Cheng et al., 1996, Proc. Natl. Acad.

Sci. USA 93:3636-3641; Staal et al., 1987, Proc. Natl. Acad. Sci. USA 84:5034-5037; Li et al., 2005, World J. Gastroenterol. 11:285-288; Li et al., 1997, Science 275:1943-1947; Goel et al., 2004, 64:3014-3021). PI3K pathway activation can be assessed by immunohistochemical analysis of PTEN or phosphorylated AKT levels in clinical samples (Slipicevic et al., 2005, Am. J. Clin. Pathol. 124:528-536). Molecular targets of such inhibitors include, but are not limited to, PI3K, AKT, mTORC1, mTORC2, PDK1, MYC, cMET, FGFR2, growth factors (EGF, b-FGF, IGF1, Insulin, or Heregulin) and the like. Other molecular targets are well known in the art and are described, for example, in US 2011-0015869.

Exemplary inhibitors of PI3K/AKT signaling are also well known in the art and include, but are not limited to: phosphatidylinositol ether lipid analogs, allosteric AKT inhibitors, HSP90 inhibitor, alkylphospholipid perifosine, rapamycin, RAD001, FTY720, PDK1 inhibitors (BX-795, BX-912, and BX-320 (Feldman et al., 2005, J. Biol. Chem. 280:19867-19874); 7-hydroxystaurosporine (Sato et al., 2002, Oncogene, 21:1727-1738)); PI3K inhibitors (wortmannin (Wymann et al., 1996, Mol. Cell. Biol. 16:1722-1733); LY294002 (Vlahos et al., 1994, J. Biol. Chem. 269:5241-5248; Wetzker and Rommel, 2004, Curr. Pharm. Des. 10:1915-1922); IC87114 (Finan and Thomas, 2004, Biochem. Soc. Trans. 32:378-382; WO0181346); WO01372557; U.S. Pat. No. 6,403,588; WO0143266); AKT antibodies (Shin et al., 2005, Cancer Res. 65:2815-2824) (see also Cheng et al., Oncogene, 2005, 24:7482-7492 for review on inhibitors of AKT pathway), and IGF1R inhibitors (such as monoclonal antibody MK-0646 U.S. Pat. No. 7,241,444). The inhibitors and agents listed in the Examples section that were used to identify and refine the growth factor signaling pathway biomarkers are also exemplary growth factor pathway agents (i.e., AKT1/2 inhibitors L-001154547 ('547; 3-phenyl-2-(4-{[4-(5-pyridin-2-yl-1H-1,2,4-triazol-3-yl)piperidin-1-yl]me-thyl}phenyl)-1,6-naphthyridin-5(6H)-one; disclosed in WO2006065601), L-01173931 ('931; 6-Methyl-3-phenyl-2-(4-{[4-(5-pyridin-2-yl-1H-1,2,4-triazol-3-yl)piperidi-n-1-yl]-methyl}phenyl)-1,6-naphthyridin-5(6H)-one; disclosed in WO2006065601; gamma secretase inhibitor 421B (U.S. Pat. No. 7,138,400 and WO02/36555); cMET inhibitors L-001501404 (4-(6-Phenyl-[1,2,4]triazolo[4,3-b][1,2,4]triazin-3-ylmethyl)-phenol, see also U.S. Pat. No. 7,122,548), MK-2461 (N-[(2R)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide), and L-001793225 (1-[3-(1-Methyl-1H-pyrazol-4-yl)-5-oxo-5H-benzo[4,5]cyclohepta[1,2-b]pyri-din-7-yl]-N-(pyridin-2-ylmethyl)methanesulfonamide.

In still another embodiment, the pro-survival pathway is the MEK/ERK signaling pathway. The extracellular signal-regulated kinases (ERKs) are activated by multiple signals including growth factors, cytokines, transforming growth factors, and G protein-coupled receptors. These signals lead to activation of RAS small G proteins which activate RAF kinases. Active RAF kinases phosphorylate and activate MEK kinases, which subsequently phosphorylate and activate ERK1/2 kinases. ERK1/2 kinases phosphorylate and regulate numerous substrates including other protein kinases, protein phosphatases, transcription factors, scaffolding proteins, signaling molecules and apoptosis-related proteins which lead to a variety of cell type and context-dependent responses. Constitutive activation of ERK1/2 by activating mutations in NRAS or BRAF is observed in the majority of melanomas and plays an integral role in the regulation of proliferation, invasiveness, and survival. In one embodiment, "ERK signaling" is signaling involving or mediated by the kinase activity of ERK1/2 kinases. In another embodiment, ERK signaling comprises signal transduction via downstream targets of ERK1/2 kinase activity. Components of the ERK signaling pathway are known to those of ordinary skill in the art. For example, in humans, components of the ERK signaling pathway that can positively regulate ERK signaling include, for example, BRAF (NCBI Gene ID No: 673); EGFR (NCBI Gene ID No: 1956); HER2 (NCBI Gene ID No: 2064); c-KIT (NCBI Gene ID No: 3815); MET (NCBI Gene ID No: 4233); MEK1 (NCBI Gene ID No: 5604); MEK2 (NCBI Gene ID No: 5605); ERK1 (NCBI Gene ID No: 5595); ERK2 (NCBI Gene ID No: 5594); HRAS (NCBI Gene ID No: 3265); KRAS (NCBI Gene ID No: 3845); and NRAS (NCBI Gene ID No: 4893).

An inhibitor of ERK signaling can be an antagonist of any component of the ERK signaling pathway that positively regulates ERK signaling, e.g. BRAF or MEK, or an agent which decreases the amount or activity of those components, e.g. an RNAi molecule. An inhibitor of ERK signaling can be an agonist of any component of the ERK signaling pathway which negatively regulates ERK signaling, or an agent which increases the amount or activity of those components. In some embodiments, an inhibitor of ERK signaling specifically inhibits the kinase activity of one or more RAF kinases or an ortholog thereof, e.g., it decreases the phosphorylation of one or more MEK kinases. In some embodiments, an inhibitor of ERK signaling is a specific inhibitor of the activity of BRAF. In some embodiments, an inhibitor of ERK signaling is a specific inhibitor of the activity of a mutant form of BRAF. In some embodiments, an inhibitor of ERK signaling is a specific inhibitor of the activity of BRAF.sup.V600E. In some embodiments, an inhibitor of ERK signaling specifically inhibits the kinase activity of one or more MEK kinase or an ortholog thereof, e.g., it decreases the phosphorylation of ERK1/2. In some embodiments, an inhibitor of ERK signaling specifically inhibits the kinase activity of one or more of ERK1 and ERK2 kinases or an ortholog thereof, e.g., it decreases the phosphorylation of a substrate of ERK1/2. Inhibition of ERK signaling can be measured according to methods well-known to those of ordinary skill in the art. By way of non-limiting example, inhibition of ERK signaling can be measured by determining the level of dual-phosphorylated ERK1/2 (ppERK1/2) as described in detail elsewhere herein. In brief, the level of ppERK1/2 can be detected by immunoblot assay. Contacting a cell with an agent that is an inhibitor of ERK signaling will cause the cell to exhibit a lower level of ppERK1/2 than a cell not contacted with the agent. Components of the ERK signaling pathway that can negatively regulate ERK signaling include, for example, SGK1 (NCBI Gene ID No: 6446); IGFBP7 (NCBI Gene ID No: 3490); SPRED1 (NCBI Gene ID No: 161742); and KSR1 (NCBI Gene ID No: 8844).

In some embodiments, the inhibitor of ERK signaling can be an inhibitor of MEK. As used herein, the term "inhibitor of MEK" refers to a compound or agent, such as a small molecule, that inhibits, decreases, lowers, or reduces the activity of MEK. Examples of inhibitors of MEK include, but are not limited to, AZD6244 (6-(4-Bromo-2-chlorophenylamino)-7-fluoro-3-methyl-3H-benzoimida-zole-5-carboxylic acid (2-hydroxy-ethoxy)-amide; selumetinib; Structure IV), and U0126 (1,4-diamino-2,3-dicyano-1,4-bis [2-aminophenylthio]butadiene; ARRY-142886; Structure V). Further non-limiting examples of MEK inhibitors include PD0325901, AZD2171, GDC-0973/XL-518, PD98059, PD184352, GSK1120212, RDEA436, RDEA119/BAY869766, AS703026, BIX 02188, BIX 02189, CI-1040 (PD184352), PD0325901, and PD98059. These and other inhibitors of MEK, as well as non-limiting examples of their methods of manufacture, are described in U.S. Pat. Nos. 5,525,625; 6,251,943; 7,820,664; 6,809,106; 7,759,518; 7,485,643; 7,576,072; 7,923,456; 7,732,616; 7,271,178; 7,429,667; 6,649,640; 6,495,582; 7,001,905; US Patent Publication No. US2010/0331334, US2009/0143389, US2008/0280957, US2007/0049591, US2011/0118298, International Patent Application Publication No. WO98/43960, WO99/01421, WO99/01426, WO00/41505, WO00/42002, WO00/42003, WO00/41994, WO00/42022, WO00/42029, WO00/68201, WO01/68619, WO02/06213 and WO03/077914, the contents of which are herein incorporated by reference in their entireties.

In another embodiment, a therapeutic agent is an inhibitor of EGFR. Epidermal Growth Factor Receptor (EGFR) is a member of the type 1 subgroup of receptor tyrosine kinase family of growth factor receptors which play critical roles in cellular growth, differentiation and survival. Activation of these receptors typically occurs via specific ligand binding which results in hetero- or homodimerization between receptor family members, with subsequent autophosphorylation of the tyrosine kinase domain. Specific ligands which bind to EGFR include epidermal growth factor (EGF), transforming growth factor alpha (TGF alpha), amphiregulin and some viral growth factors. Activation of EGFR triggers a cascade of intracellular signaling pathways involved in both cellular proliferation (the ras/raf/MAP kinase pathway) and survival (the PI3 kinase/Akt pathway). Members of this family, including EGFR and HER2, have been directly implicated in cellular transformation. A number of human malignancies are associated with aberrant or overexpression of EGFR and/or overexpression of its specific ligands. Gullick, Br. Med. Bull. (1991), 47:87-98; Modijtahedi & Dean, Int. J. Oncol. (1994), 4:277-96; Salomon, et al., Crit. Rev. Oncol. Hematol. (1995), 19:183-232. Aberrant or overexpression of EGFR has been associated with an adverse prognosis in a number of human cancers, including head and neck, breast, colon, prostate, lung (e.g., NSCLC, adenocarcinoma and squamous lung cancer), ovarian, gastrointestinal cancers (gastric, colon, pancreatic), renal cell cancer, bladder cancer, glioma, gynecological carcinomas and prostate cancer. In some instances, overexpression of tumor EGFR has been correlated with both chemoresistance and a poor prognosis. Lei, et al., Anti-cancer Res. (1999), 19:221-28; Veale, et al., Br. J. Cancer (1993); 68:162-65. Mutations in EGFR are associated with many types of cancer as well. For example, EGFR mutations are highly prevalent in non-mucinous BAC patients. Finberg, et al., J. Mol. Diagnostics. (2007) 9(3):320-26. In an embodiment the EGFR inhibitor is an antibody such as Erbitutux™ (cetuximab, Imclone Systems Inc.) and ABX-EGF (panitumumab, Abgenix, Inc.). In another embodiment the EGFR inhibitor is a small molecule that competes with ATP such as Tarceva™ (erlotinib, OSI Pharmaceuticals), Iressa™ (gefitinib, Astra-Zeneca), tyrphostins described by Dvir, et al., J Cell Biol., 113:857-865 (1991); tricyclic pyrimidine compounds disclosed in U.S. Pat. No. 5,679,683; compound 6-(2,6-dichlorophenyl)-2-(4-(2-diethylaininoethoxy)phenylamino)-8-methyl-8H-pyrido(2,3-d)pyrimidin-7-one (known as PD166285) disclosed in Panek, et al., Journal of Pharmacology and Experimental Therapeutics 283, 1433-1444 (1997).

In addition to the specific agents described above, it is further contemplated that a polypeptide, an antibody or antigen binding fragment thereof, a toxin, an RNA interfering molecule, an siRNA molecule, and shRNA molecule, an antisense oligonucleotide, a peptide, a peptidomimetic, an aptamer, and the like, as well as combinations thereof, that appropriately enhance or inhibit the targets of pro-survival signaling pathways can also be used as a therapeutic agent according to the present invention. In particular, the nucleic acid sequence, amino acid sequence, functional domain, structural domain, gene locus, and other identifying information for the signaling pathway targets described herein are well known in the art. For example, KRAS nucleic acid and amino acid sequences from many organisms is well known in the art and include, for example, canine KRAS (NCBI Accession XM_540523.3, XP_540523.3, XM_003432429.1, and XP_00343247.1), chimpanzee KRAS (NCBI Accession XM_003313794.1, XP_003313842.1, XM_528758.3, and XP_528758.3), cow KRAS (NCBI Accession NM_001110001.1 and NP_001103471.1), mouse KRAS (NCBI Accession NM_021284.6 and NP_067259.4), rat KRAS (NCBI Accession NM_031515.3 and NP_113703.1), chicken KRAS (NCBI Accession NM_001256162.1 and NP_001243091.1), and zebrafish KRAS (NCBI Accession NM_001003744.1 and NP_001003744.1). Human KRAS sequences include the following:

KRAS isoform a coding nucleic acid sequence (NCBI Accession NM_033360.2):

```
                                                          (SEQ ID NO: 1)
  1 atgactgaat ataaacttgt ggtagttgga gctggtggcg taggcaagag tgcctttgacg 61 atacagctaa ttcagaatca ttttgtggac gaatatgatc caacaataga ggattcctac 121 aggaagcaag tagtaattga tggagaaacc tgtctcttgg atattctcga cacagcaggt 181 caagaggagt acagtgcaat gagggaccag tacatgagga ctggggaggg ctttctttgt 241 gtatttgcca taaataatac taaatcattt gaagatattc accattatag agaacaaatt 301 aaaagagtta aggactctga agatgtacct atggtcctag taggaaataa atgtgatttg 361 ccttctagaa cagtagacac aaaacaggct caggacttag caagaagtta tggaattcct 421 tttattgaaa catcagcaaa gacaagacag agagtggagg atgcttttta tacattggtg 481 agggagatcc gacaatacag attgaaaaaa atcagcaaag aagaaaagac tcctggctgt 541 gtgaaaatta aaaaatgcat tataatgtaa
```

KRAS isoform an amino acid sequence (NCBI Accession NP_203524.1):

(SEQ ID NO: 2)

```
  1 mteyklvvvg aggvgksalt iqliqnhfvd eydptiedsy rkqvvidget clldildtag 61 qeeysamrdq ymrtgegflc vfainntksf edihhyreqi krvkdsedvp mvlvgnkcdl 121 psrtvdtkqa qdlarsygip fietsaktrq rvedafytlv reirqyrlkk iskeektpgc 181 vkikkciim
```

KRAS isoform b coding nucleic acid sequence (NCBI Accession NM_004985.31:

(SEQ ID NO: 3)

```
  1 atgactgaat ataaacttgt ggtagttgga gctggtggcg taggcaagag tgccttgacg 61 atacagctaa ttcagaatca ttttgtggac gaatatgatc aacaataga ggattcctac 121 aggaagcaag tagtaattga tggagaaacc tgtctcttgg atattctcga cacagcaggt 181 caagaggagt acagtgcaat gagggaccag tacatgagga ctggggaggg ctttctttgt 241 gtatttgcca taaataatac taaatcattt gaagatattc accattatag agaacaaatt 301 aaaagagtta aggactctga agatgtacct atggtcctag taggaaataa atgtgatttg 361 ccttctagaa cagtagacac aaaacaggct caggacttag caagaagtta tggaattcct 421 tttattgaaa catcagcaaa gacaagacag ggtgttgatg atgccttcta tacattagtt 481 cgagaaattc gaaaacataa agaaaagatg agcaaagatg gtaaaaagaa gaaaaagaag 541 tcaaagacaa agtgtgtaat tatgtaa
```

KRAS isoform b amino acid sequence (NCBI Accession NP_004976.2):

(SEQ ID NO: 4)

```
  1 mteyklvvvg aggvgksalt iqliqnhfvd eydptiedsy rkqvvidget clldildtag 61 qeeysamrdq ymrtgegflc vfainntksf edihhyreqi krvkdsedvp mvlvgnkcdl 121 psrtvdtkqa qdlarsygip fietsaktrq gvddafytlv reirkhkekm skdgkkkkkk 181 sktkcvim
```

In certain embodiments, the KRAS pathway is involved. Growth factor receptors are coupled to activation of the small GTPase protein, Ras (KRAS in humans). Activated KRAS subsequently initiates a kinase cascade by activating Raf (a kinase) which then phosphorylates (activates) MEK1/2, which in turn phosphorylates (activates) ERK1/2, which itself phosphorylates or activates transcription factors to change or enhance expression of genes involved in proliferation. The vast majority (90%) of pancreatic tumors harbor activating KRAS mutations. This causes constitutive activation of the downstream processes, bypassing the need for upstream growth factor receptor activation. This perpetuates the "running motor" of the pancreatic cancer cell. KRAS mutations have the effect of rendering these tumors resistant to agents that inhibit growth factor receptor activity, specifically the biologic anti-EGFR agent, Cetuximab.

C. Vesicles

As used herein, "lipid" refers to an agent exhibiting amphipathic characteristics that cause it to spontaneously adopt an organized structure in water wherein the hydrophobic portion of the molecule is sequestered away from the aqueous phase. A lipid in the sense of this invention is any substance with characteristics similar to those of fats or fatty materials. As a rule, molecules of this type possess an extended apolar region and, in the majority of cases, also a water-soluble, polar, hydrophilic group, the so-called head-group. Phospholipids are lipids which are the primary constituents of cell membranes. Typical phospholipid hydrophilic groups include phosphatidylcholine and phosphatidylethanolamine moieties, while typical hydrophobic groups include a variety of saturated and unsaturated fatty acid moieties, including diacetylenes. Mixture of a phospholipid in water causes spontaneous organization of the phospholipid molecules into a variety of characteristic phases depending on the conditions used. These include bilayer structures in which the hydrophilic groups of the phospholipids interact at the exterior of the bilayer with water, while the hydrophobic groups interact with similar groups on adjacent molecules in the interior of the bilayer. Such bilayer structures can be quite stable and form the principal basis for cell membranes.

Bilayer structures can also be formed into closed spherical shell-like structures which are called vesicles or liposomes. The liposomes employed in the present invention can be prepared using any one of a variety of conventional liposome preparatory techniques. As will be readily apparent to those skilled in the art, such conventional techniques include sonication, chelate dialysis, homogenization, solvent infusion coupled with extrusion, freeze-thaw extrusion, microemulsification, as well as others. These techniques, as well as others, are discussed, for example, in U.S. Pat. No. 4,728,578, U.K. Patent Application G.B. 2193095 A, U.S. Pat. No. 4,728,575, U.S. Pat. No. 4,737,323, International Application PCT/US85/01161, Mayer et al., Biochimica et Biophysica Acta, Vol. 858, pp. 161-168 (1986), Hope et al., Biochimica et Biophysica Acta, Vol. 812, pp. 55-65 (1985), U.S. Pat. No. 4,533,254, Mahew et al., Methods In Enzymology, Vol. 149, pp. 64-77 (1987), Mahew et al., Biochimica et Biophysics Acta, Vol. 75, pp. 169-174 (1984), and Cheng et al., Investigative Radiology, Vol. 22, pp. 47-55. (1987), and U.S. Ser. No. 428,339, filed Oct. 27, 1989. The disclosures of each of the foregoing patents, publications and patent applications are incorporated by reference herein, in their entirety. A solvent free system similar to that described in International Application PCT/US85/01161, or U.S. Ser. No. 428,339, filed Oct. 27, 1989, may be employed in preparing the liposome constructions. By following these procedures, one is able to prepare liposomes having encapsulated therein a gaseous precursor or a solid or liquid contrast enhancing agent.

The materials which may be utilized in preparing the liposomes of the present invention include any of the materials or combinations thereof known to those skilled in the art as suitable in liposome construction. The lipids used may be of either natural or synthetic origin. Such materials include, but are not limited to, lipids with head groups including phosphatidylcholine, phosphatidylethanolamine, phosphatidylserine, phosphatidylglycerol, phosphatidic acid, phosphatidylinositol. Other lipids include lysolipids, fatty acids, sphingomyelin, glycosphingolipids, glucolipids, glycolipids, sulphatides, lipids with amide, ether, and ester-linked fatty acids, polymerizable lipids, and combinations thereof. Additionally, liposomes may include lipophilic compounds, such as cholesterol. As one skilled in the art will recognize, the liposomes may be synthesized in the absence or presence of incorporated glycolipid, complex carbohydrate, protein or synthetic polymer, using conventional procedures. The surface of a liposome may also be modified with a polymer, such as, for example, with polyethylene glycol (PEG), using procedures readily apparent to those skilled in the art. Lipids may contain functional surface groups for attachment to a metal, which provides for the chelation of radioactive isotopes or other materials that serve as the therapeutic entity. Any species of lipid may be used, with the sole proviso that the lipid or combination of lipids and associated materials incorporated within the lipid matrix should form a bilayer phase under physiologically relevant conditions. As one skilled in the art will recognize, the composition of the liposomes may be altered to modulate the biodistribution and clearance properties of the resulting liposomes.

The membrane bilayers in these structures typically encapsulate an aqueous volume, and form a permeability barrier between the encapsulated volume and the exterior solution. Lipids dispersed in aqueous solution spontaneously form bilayers with the hydrocarbon tails directed inward and the polar headgroups outward to interact with water. Simple agitation of the mixture usually produces multilamellar vesicles (MLVs), structures with many bilayers in an onion-like form having diameters of 1-10 .mu.m (1000-10,000 nm). Sonication of these structures, or other methods known in the art, leads to formation of unilamellar vesicles (UVs) having an average diameter of about 30-300 nm. However, the range of 50 to 200 nm is considered to be optimal from the standpoint of, e.g., maximal circulation time in vivo. The actual equilibrium diameter is largely determined by the nature of the phospholipid used and the extent of incorporation of other lipids such as cholesterol. Standard methods for the formation of liposomes are known in the art, for example, methods for the commercial production of liposomes are described in U.S. Pat. No. 4,753,788 to Ronald C. Gamble and U.S. Pat. No. 4,935,171 to Kevin R. Bracken.

Either as MLVs or UVs, liposomes have proven valuable as vehicles for drug delivery in animals and in humans. Active drugs, including small hydrophilic molecules and polypeptides, can be trapped in the aqueous core of the liposome, while hydrophobic substances can be dissolved in the liposome membrane. Radioisotopes may be attached to the surfaces of vesicles and isotope-chelator complexes may be encapsulated in the interior of the vesicles. Other molecules, such as DNA or RNA, may be attached to the outside of the liposome for gene therapy applications. The liposome structure can be readily injected and form the basis for both sustained release and drug delivery to specific cell types, or parts of the body. MLVs, primarily because they are relatively large, are usually rapidly taken up by the reticuloendothelial system (the liver and spleen). The invention typically utilizes vesicles which remain in the circulatory system for hours and break down after internalization by the target cell. For these requirements the formulations preferably utilize UVs having a diameter of less than 200 nm, preferably less than 100 nm.

D. Pharmaceutical Compositions

In another aspect, the present invention provides pharmaceutically acceptable compositions which comprise a therapeutically-effective amount of agents described herein, e.g., a chemotherapeutic agent, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The term "administering" is intended to include routes of administration which allow the compositions described herein to perform their intended functions of treating cancer or inhibiting cancer cell growth. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the therapeutic agents can be coated with or disposed in a selected material to protect it from natural conditions which may detrimentally effect its ability to perform its intended function. The therapeutic agents can be administered alone, or in conjunction with a pharmaceutically acceptable carrier. Further the therapeutic agents can be administered as a mixture of therapeutic agents, which also can be coadministered with a pharmaceutically acceptable carrier.

As used herein, an "effective amount," when used with respect to the combination of agents described herein includes, without limitation, an amount of each agent in the combination that provides a statistically significant desired effect on cancer cells. In some embodiments, the effect amount can be narrowed to further require clinical acceptability of the amount of toxicity to non-cancer cells. Representative desired effects are described herein. For example, the effect can be a decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), a statistically significant increase in survival relative to treatment with individual agents of the combination or subcombinations of the combination alone, and the like. The effective amount can vary depending on such factors as the type of cell growth being treated or inhibited, the type of therapeutic agent(s) employed, the particular therapeutic agent, the size of the subject, or the severity of the cancer cell growth or tumor. For example, the choice of each of the individual agents which make up the combination can affect what constitutes an "effective amount". One of ordinary skill in the art would be able to study the aforementioned factors and make the determination regarding the effective amount of the combination of the therapeutic agents without undue experimentation.

For example, an in vitro assay can be used to determine an "effective amount" of the therapeutic agents. The ordinarily skilled artisan would select an appropriate amount of each individual agent in the combination for use in the aforementioned in vitro assay. The cell survival fraction can be used to determine whether the selected amounts were an "effective amount" for the particular combination of therapeutic agents. For example, the selected amounts used within the assay preferably should result in a killing of at least 50% of the cells, more preferably 75%, and most preferably at least 95%. In an embodiment, the effective dose of the therapeutic agent is a subtoxic dose. As used herein, the term subtoxic dose refers to a dose which results in the killing of less than about 10% of the cells.

The regimen (e.g., order) of administration can also affect what constitutes an effective amount. Further, several divided dosages, as well as staggered dosages, can be administered daily or sequentially, or the dose can be continuously infused. Further, the dosages can be proportionally increased or decreased as indicated by the exigencies of the therapeutic situation.

The phrase "pharmaceutically acceptable" is employed herein to refer to those combinations of therapeutic agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the therapeutic agents encompassed by the invention. These salts can be prepared in situ during the final isolation and purification of the therapeutic agents, or by separately reacting a purified therapeutic agents in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

In other cases, the therapeutic agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of therapeutic agents. These salts can likewise be prepared in situ during the final isolation and purification of the therapeutic agents, or by separately reacting the purified therapeutic agents in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, from about 5 percent to about 70 percent, or from about 10 percent to about 30 percent.

Methods of preparing these formulations or compositions include the step of bringing into association a therapeutic agent with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and *acacia* or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and *acacia*) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or *acacia*; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active therapeutic agents may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of a therapeutic agent include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a therapeutic agent, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The therapeutic agent can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of a therapeutic agent in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the therapeutic agents of the present invention are administered as pharmaceuticals, to humans and animals, they can be given per se or as a pharmaceutical composition containing, for example, 0.1 to 99.5% (or 0.5 to 90%) of active ingredient in combination with a pharmaceutically acceptable carrier.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

III. Anti-Cancer Methods

The methods of the present invention relate to therapeutic and prophylactic compositions for treating cancer or preventing the growth of cancer cells, e.g., tumor growth in a subject. The compositions of the present invention include an effective amount of ceramide (e.g., C6-ceramide) and an effective amount of one or more anti-cancer agents in an effective amount of a vesicle.

In another aspect, the invention relates to methods for treating cancer, e.g., inhibiting tumor growth, in a subject by administering to a subject an effective amount of a ceramide (e.g., C6-ceramide) and an effective amount of a therapeutic agent, e.g., a chemotherapeutic agent, in an effective amount of a vesicle, wherein the ceramide and the other components of the vesicle allow for a reduction in the amount of the therapeutic agent(s) required to be effective, resulting in fewer side effects in the subject being treated.

In general, the methods of the present invention include a step of contacting cancer cells with vesicle comprising a combination of a ceramide (e.g., C6-ceramide) and a therapeutic agent, e.g., a chemotherapeutic agent, in an amount effective for promoting apoptosis or cell death. In some embodiments, the cancer cells can harbor activating KRAS mutations. In other embodiments, the cancer cells do not harbor activating KRAS mutations.

As used herein, the term "cell death" includes the processes by which mammalian cells die or become terminally differentiated. Such processes include apoptosis (both reversible and irreversible) and processes thought to involve apoptosis (e.g., cell senescence), as well as necrosis and terminal cell differentiation. "Cell death" is used herein to refer to the death or imminent death of nucleated cells (e.g., neurons, myocytes, hepatocytes and the like) as well as to the death or imminent death of anucleate cells (e.g., red blood cells, platelets, and the like). Cell death is typically manifested by the exposure of the internal membrane phospholipid phosphatidylserine (PS) on the outer leaflet of the plasma membrane and can be detected by art recognized methods.

As used herein the term "apoptosis" includes programmed cell death which can also be detected using techniques which are known in the art. For example, apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage. Apoptosis can be measured in the presence or the absence of Fas-mediated signals. In one embodiment, cytochrome C release from mitochondria during cell apoptosis can be detected, e.g., plasma cell apoptosis (as described in, for example, Bossy-Wetzel E. et al. (2000) *Methods in Enzymol.* 322:235-42). Other assays include: cytofluorometric quantitation of nuclear apoptosis induced in a cell-free system (as described in, for example, Lorenzo H. K. et al. (2000) *Methods in Enzymol.* 322:198-201); apoptotic nuclease assays (as described in, for example, Hughes F. M. (2000) *Methods in Enzymol.* 322:47-62); analysis of apoptotic cells, e.g., apoptotic plasma cells, by flow and laser scanning cytometry (as described in, for example, Darzynkiewicz Z. et al. (2000) *Methods in Enzymol.* 322:18-39); detection of apoptosis by annexin V labeling (as described in, for example, Bossy-Wetzel E. et al. (2000) *Methods in Enzymol.* 322:15-18); transient transfection assays for cell death genes (as described in, for example, Miura M. et al. (2000) *Methods in Enzymol.* 322:480-92); and assays that detect DNA cleavage in apoptotic cells, e.g., apoptotic plasma cells (as described in, for example, Kauffman S. H. et al. (2000) *Methods in Enzymol.* 322:3-15). Apoptosis can also be measured by propidium iodide staining or by TUNEL assay.

In another aspect, the invention features methods for inhibiting the proliferation of cancer cells by contacting the cells with a vesicle comprising a ceramide (e.g., C6-ceramide) and a therapeutic agent(s). In general, the method includes a step of contacting cancer cells with a vesicle comprising ceramide (e.g., C6-ceramide) and a therapeutic agent(s) effective for reducing the proliferation of cancer cells. The reduced proliferation of cancer cells can be detected by at least one of the following biological activities: (1) a decrease in solid tumor cell proliferation; (2) a decrease in the fraction of cells in the DNA synthesis phase of the cell cycle (S-phase); (3) an increase in expression of differentiation-associated markers; (4) a decrease in the expression of proliferation-associated markers such as Ki-67 (MIB-1), e.g., a decrease in the expression of Ki-67 by about 30-50%, using techniques which are known in the art. Changes in expression can occur in the protein or mRNA levels.

The present method can be performed on cells in culture, e.g., ex vivo, or can be performed on cells present in an animal subject, e.g., as part of an in vivo therapeutic protocol. The therapeutic regimen can be carried out on a human or other animal subject.

The methods of the present invention allow for a reduction in the amount of the therapeutic agent, e.g., a chemotherapeutic agent, required to be effective, resulting in fewer side effects in the subject being treated.

In one embodiment, the cells to be treated are pancreatic cancer and/or colorectal cancer cells. For instance, the instant method can be carried out to prevent the proliferation of a pancreatic cancer and/or colorectal cancer cell tumor.

Determination of a therapeutically amount of a phospholipid, a therapeutically effective amount of a ceramide (e.g., C6-ceramide), and a therapeutically effective amount of a therapeutic agent, e.g., a chemotherapeutic agent, can be readily made by the physician (the "attending clinician"), as one skilled in the art, by the use of known techniques and by observing results obtained under analogous circumstances. The dosages may be varied depending upon the requirements of the patient in the judgment of the attending clinician, the severity of the condition being treated and the particular compound being employed. In determining the therapeutically effective amount or dose, a number of factors are considered by the attending clinician, including, but not limited to: the specific hyperplastic/neoplastic cell involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment; and other relevant circumstances. U.S. Pat. No. 5,427,916, for example, describes method for predicting the effectiveness of antineoplastic therapy in individual patients, and illustrates certain methods which can be used in conjunction with the treatment protocols of the instant invention.

The effectiveness of any particular combination of a ceramide (e.g., C6-ceramide) with a therapeutic agent(s) to treat cancer can be monitored by comparing two or more samples obtained from a patient undergoing anti-cancer treatment. In general, it is preferable to obtain a first sample from the patient prior to beginning therapy and one or more samples during treatment. In such a use, a baseline of expression of cancer cells prior to therapy is determined and then changes in the baseline state of expression of cancer cells is monitored during the course of therapy. Alternatively, two or more successive samples obtained during treatment can be used without the need of a pre-treatment baseline sample. In such a use, the first sample obtained from the subject is used as a baseline for determining whether the expression of cancer cells is increasing or decreasing.

In general, when monitoring the effectiveness of a therapeutic treatment, two or more samples from the patient are examined. Preferably, three or more successively obtained samples are used, including at least one pretreatment sample.

EXAMPLES

Example 1: Materials and Methods Used in Examples 2-3

A. Chemicals and Reagents

Paclitaxel, cetuximab, and gemcitabine were obtained from Roger Williams Medical Center, Providence, R.I. (#1) DOPC (1,2-dioleoyl-sn-glycero-3-phosphocholine); (#3) DSPC (1,2-distearoyl-sn-glycero-3-phosphocholine); (#5) DPGG (1,2-dipalmitoyl-sn-glycero-3-galloyl); (#7) 18:0 PEG2 PE (1,2-distearoyl-sn-glycero-3-phosphoethanolamine-N-[methoxy(polyethylene glycol)-2000]); and C6-ceramide (N-hexanoyl-D-sphingosine, CAS NO. 124753-97-5) were obtained from Avanti Polar Lipids (Alabaster, Ala.).

B. Cell Culture

Pancreatic cancer cell lines L3.6, PanC-1 and MIA-PaCa2 cells (MIA) were maintained in DMEM medium (Sigma, St. Louis, Mo.), supplemented with 10% fetal bovine serum (Invitrogen, Carlsbad, Calif.), Penicillin/Streptomycin (1:100, Sigma, St. Louis, Mo.) and 4 mM L-glutamine (Sigma, St. Louis, Mo.), in a $CO_2$ incubator at 37° C.

C. Cell Viability Assay

Cell viability was measured by the 3-[4,5-dimethylthiazol-2-y]-2,5-diphenyltetrazolium bromide (MTT) method, as described in Cao et al. (2009) *Sci. Signal.* 2:RA17. Briefly, the cells were collected and seeded in 96-well plate at a density of $2 \times 10^5$ cells/$cm^2$. Different seeding densities were optimized at the beginning of the experiments. After overnight incubation cells were exposed to fresh medium containing indicated reagents at 37° C. After incubation for different time periods, 20 µl of MTT tetrazolium (Sigma, St. Louis, Mo.) salt dissolved in Hank's balanced salt solution at a concentration of 5 mg/ml was added to each well and incubated in a $CO_2$ incubator for an additional 4 hours. The medium was subsequently aspirated from each well and 150 µl of DMSO (Sigma, St. Louis, Mo.) was added to dissolve formazan crystals and the absorbance of each well was obtained using a Dynatech MR5000 plate reader at a test wavelength of 490 nm with a reference wavelength of 630 nm.

Example 2: Formulation of Therapeutic Vesicles and Physical Properties

Ceramide liposomes and control liposomes were prepared as described previously in Stover et al., *J. Pharmacol. Exp. Ther.* (2003), 307:468-475. Briefly, lipids, dissolved in chloroform ($CHCl_3$), were combined in specific molar ratios, dried under a stream of nitrogen ($N_2$) above lipid transition temperatures, and hydrated with steril phosphate-buffered saline (PBS). Control liposomes (non C6-Ceramide) contained a molar ratio of lipids equivalent to that of the ceramide liposomal formulations. The resulting solution was sonicated for 2 min and then extruded through a 100 nm polycarbonate membrane. The liposomes were kept at 4° C. in PBS at a concentration of 1 µg/ml prior to use Liposomal preparations are listed in Table 2. Fractions 1, 3, 5, and 7 include C6-Ceramide. Fractions 2, 4, 6, 8 are without C6-Ceramide.

acid, bind and precipitate a variety of lipids, proteins and polymers, DPGG bilayers appear likely to bind and tether proteins and membranes.

DPGG was shown by x-ray diffraction experiments to hydrate by forming gel phase bilayers at 20° C. with extremely narrow inter bilayer fluid separations. This indicates that opposing DPGG bilayers strongly adhere to each other. Differential scanning calorimetry shows that fully hydrated DPGG exhibits a pretransition exotherm (3.7 kcal/mol at 52° C.) and a high enthropy (11.3 kcal/mol, main endo thermic transition at 69° C.). These thermal properties are similar to those of galloyl Ceramides with similar hydrocarbon chain composition. The adhesive and thermal properties are thought to be due to intermolecular hydrogen bonding and hydrophobic interactions between the aromatic rings on gallic acids.

18:0 PEG2 PE is the industry standard which also avoids the RE system.

Example 3: Drug-Induced Cell Death in Pancreatic Cancer Cells In Vitro

Synergism among active agents, C6-ceramide, and vesicles in killing L3.6, PanC-1 and MIA cells in vitro was tested. Briefly, L3.6 cells were incubated for 18-24 hours in 1% Fetal Bovine Serum (FBS) with the liposome preparations as outlined in Example 2, Table 2 and active agents: Paclitaxel (2 µg/ml), Gemcitabine (2 µg/ml), or Cetuximab (40 µg/ml). Cell viability was determined using the MTT assay.

Fractions 1 compared to 2 and 3 compared to 4 showed no significant differences in cytotoxicity with the addition of active agents and vesicles with and without C6-Ceramide. The lack of significant differences is probably related to structural rigidity and lower miscibility of these preparations. Only fractions 5 and 7 showed significant effects. They appeared to have major influence on the responsiveness to the active agent. There was parallel hyper responsiveness with increased cytotoxicity with fractions 5 and 7 that contain C6-Ceramide. Initial screening studies showed

TABLE 2

| Preparation | Avanti Catalog# | Long Name | Fraction w/ C6 Ceramide | Fraction w/o C6 Ceramide |
|---|---|---|---|---|
| DOPC | 850375 | 1,2-dioleoyl-sn-glycero-3-phosphocholine | 1 | 2 |
| DSPC | 850365 | 1,2-distearoyl-sn-glycero-3-phosphocholine | 3 | 4 |
| DPGG | 870412 | 1,2-dipalmitoyl-sn-glycero-3-galloyl | 5 | 6 |
| 18:0 PEG2 PE | 880120 | 1,2-distearoyl-sn-glycero-3-phosphoethanolamine-N-[methoxy(polyethylene glycol)-2000] | 7 | 8 |

DOPC and DSPC preparations have rigid saturated structures requiring higher miscibility temperature (e.g., 55° C.) compared to DPGG and 18:0 PEG2 PE preparations. DOPC has a low transition temperature and is fluid at body temperature. DSPC has a high transition temperature and is rigid at body temperature.

DPGG is a lipid with a polyphenolic head group. When hydrated at room temperature, DPGG forms gel phase bilayers that strongly adhere to each other. Fraction 5 is a fluid at body temperature and induces long circulation which allows it to avoid capture by the reticuloendothelial system (RE system). Since polyphenolic compounds, such as tannic maximum enhancement of Paclitaxel with 5 (C6 Ceramide) vs #6 (control) and #7 (C6 Ceramide) vs #8 (control). Less initial activity was observed with Gemcitabine and minimal activity was observed with Cetuximab. An initial short incubation time 18-24 hours may have limited demonstration of responsiveness to Gemcitabine (cell cycle dependent) and Cetuximab (EGFR inhibitor).

Example 4: 72-Hour Cytotoxicity Study with DPGG Preparations

A more rigorous 72-hour cytotoxicity study was performed with fractions 5 and 6. Briefly, L3.6 cells were incubated for 72 hours in 5% FBS with the DPGG preparations as outlined in Example 2, Table 2 and active agents: Paclitaxel (0.1 µg/ml), Gemcitabine (5 µg/ml), or Cetuximab (25 µg/ml). Lipid molar ratios for Fraction 5 were 5:89:6 (DPGG:DOPC:C6-Ceramde) and for Fraction 6 were 5:89:6 (DPGG:DOPC:PBS). Fractions 5 and 6 were added at a concentration of 1 µg/ml. After incubation with the vesicle preparation and active agent, cell viability was determined via the MTT assay discussed in Example 1.

As shown in FIG. 1, the DPGG preparation, fractions 5 (DPGG:DOPC:C6-Ceramide) and 6 (PBS control), demonstrated significant enhancement of Taxol and Cetuximab cytotoxicity compared to incubation with active agent only (Chemo only). However, Gemcitabine showed similar cytotoxicity in presence of DPGG:DOPC with Ceramide and with control DPGG:DOPC.

Utilization of 72-hr cytotoxicity time point and chemo drug levels Taxol (0.1 µg/ml), Gem (5 µg/ml) and Cetux (25 µg/ml) resulted in more reproducible chemo toxicity results. Lipid fraction 5 demonstrated very clear demarcation of cytotoxicity with Paclitaxel and Ceramide although not with Gemcitabine where the response was similar between C6 and control. There was striking 72 hr response data with Cetuximab (67% cytotoxicity vs. 23% in control).

Example 5: 72-Hour Cytotoxicity Study with 18:0 PEG2 PE Preparations

Figure 2:
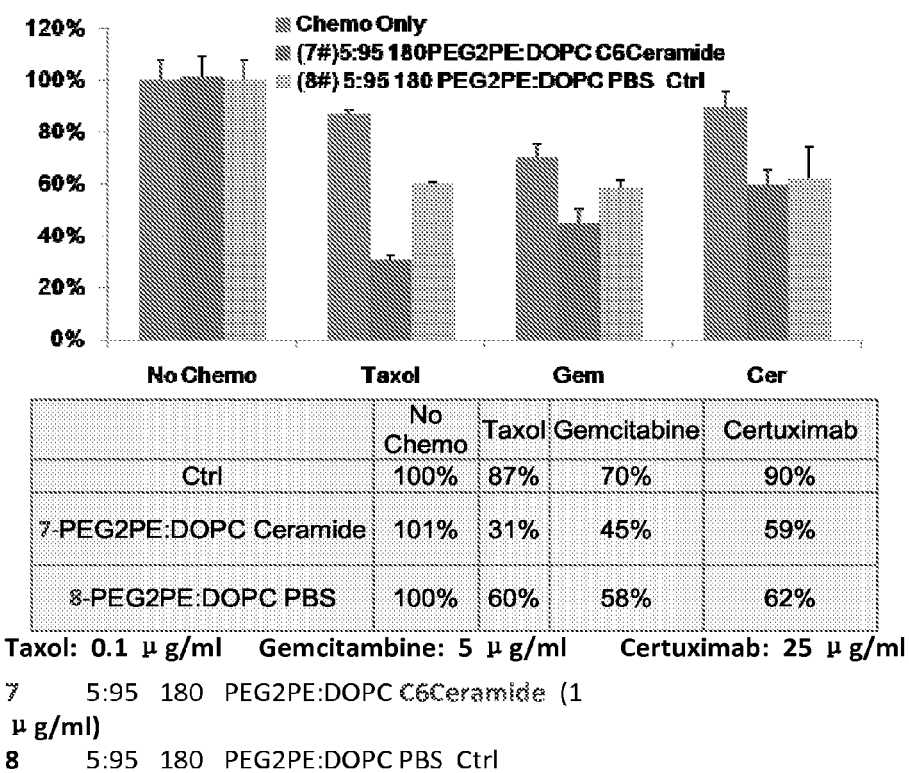
FIG. 2 depicts the sensitivity of L3.6 cells to three active agents as influenced by solubilization in #7 PEG 2PE:DOPC Ceramide vs. #8 PEG2PE:DOPC PBS. Similar to FIG. 1, percentage cell survival is shown for cells treated with vesicles and no active agent (No chemo), Paclitaxel (Taxol), gemcitabine (Gem), or cetuximab (Cer). Cell viability is noticeably reduced in the presence of an active agent with lipid vesicles that include PEG2PE, DOPC, and C6-Ceramide. Left bar=chemo only; middle bar=#7; right bar=#8.

A similar study to Example 4 was performed with the pegylated preparation (18:0 PEG2 PE). Lipid molar ratios for Fraction 7 were 5:95:1 (18:0 PEG2PE:DOPC:C6-Ceramide) and for Fraction 8 were 5:95:1 (18:0 PEG2PE:DOPC:PBS). Fractions 7 and 8 were added at a concentration of 1 µg/ml. After incubation with the vesicle preparation and active agent, cell viability was determined via the MTT assay discussed in Example 1. As shown in FIG. 2, the results parallel the DPGG preparation with Taxol (0.1 µg/ml) and Cetuximab (25 µg/ml) but showed more distinctive differences in responsiveness with Gemcitabine (5 µg/ml). Lipid Fraction #7 demonstrated strong cytotoxicity responses to C6-Ceramide vs control with Taxol in (70% cytotoxicity) and a reasonable response with Gemcitabine (55% cytotoxicity). Cetuximab showed less C6 related cytotoxicity (41% C6 vs. 38% lipid control).

Example 6: Taxol Dose Response with DPGG and PGE2PE Preparations

A dose response MTT assay demonstrated no distinctive response to C6-Ceramide combined liposome vesicles fractions 1 and 3 but did demonstrate increased cytotoxicity with fractions 5 and 7. The effect of varying dose levels of Taxol was examined using the DPGG and 18:0 PEG2 PE preparations. Briefly, L3.6 cells were incubated for 72 hours in 5% FBS with the DPGG and 18:0 PEG2 PE preparations as outlined in Example 2, Table 2 and vary concentrations of Paclitaxel (0.1 µg/ml, 0.5 µg/ml, and 1 µg/ml). Lipid molar ratios for Fraction 5 and 6 and Fractions 7 and 8 were as described in Examples 4 and 5, respectively. Cell viability was determined using the MTT assay.

Figure 3:
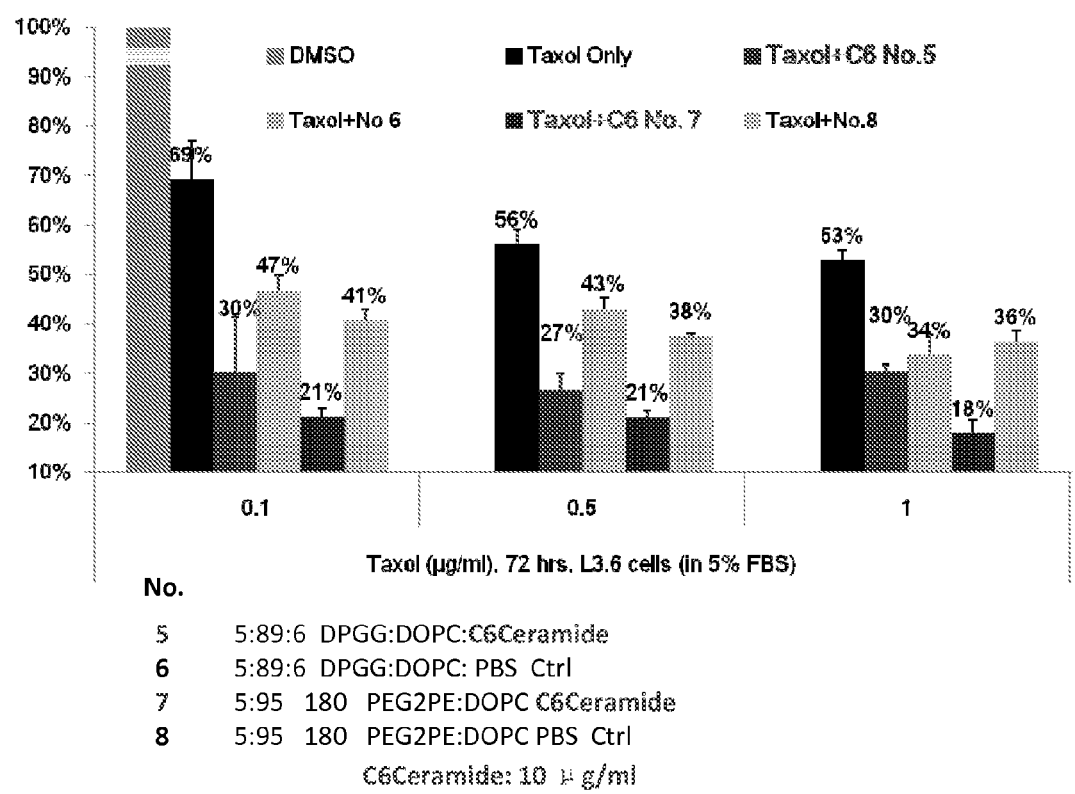
FIG. 3 depicts the sensitivity of L3.6 cells to 3 dose levels of Taxol and two lipid preparations (DPGG and PEG2PE). Percentage survival is shown for cells treated with Taxol only, Taxol and DPGG vesicle preparations with and without C6-Ceramide, and Taxol and PEG2PE preparations with and without C6-Ceramide. There are variations in Taxol induced cytotoxicity pending the solubilization method. Increasing toxicity is observed with increasing Taxol concentration but differential effects is less, i.e. at Taxol 0.1 and 0.5 μg/ml. Left bar=DMSO; $2^{nd}$ bar from the left=taxol only; $3^{rd}$ bar from the left=taxol+#5; $3^{rd}$ bar from the right=taxol+#6; $2^{nd}$ bar from the right=taxol+#7; and right bar=taxol+#8.

As shown in FIG. 3, the responsiveness with Paclitaxel (Taxol) at 3 dose levels with C6-Ceramide demonstrates clear activity of Taxol in presence of C6-Ceramide in fraction #5 (DPGG:DOPC:C6) and pegylated fraction #7 (PEG 2PE:DOPC:C6). The relative responses (i.e. % surviving cells) to Taxol+C6 vs control at the 3 dose levels of Taxol showed:

5 vs. control (6) 30% vs 47%, 27% vs. 43%, 30% vs. 34%

7 vs. control (8) 21% vs 41%, 21% vs. 38%, 18% vs. 36%

This suggests a higher cytotoxicity with Taxol in presence of the #7 preparation vs. #5 preparation. Also, the data suggest Taxol induced cytotoxicity may relate to drug dosing and to more favorable interactions with liposome C6-Ceramide as compared to the lipid fraction without C6-Ceramide. Other differences may reflect the mechanism and the drug dose level and the effect of the liposomal configuration.

The results show clearer response pattern with Taxol at dose levels of 0.1 µg/ml and 0.5 µg/ml. Although at dose level of 1 µg/ml, the response differences between C6 #5 and control is lost. With fraction 7, the differences between fractions containing C6-Ceramide and fractions without C6-Ceramide are constant at Taxol dose levels 0.1, 0.5 and 1 µg/ml.

Thus, it would appear that a chemo dose response needs to be established for each lipid fraction preparation. The other item may be the differences between the galloyl prep vs pegylated version. The anti cancer data strongly suggests benefit with both optimum lipid fraction schemes.

Example 7: Planned Animal Studies to Verify Efficacy of the Lipid Fraction #5 and #7 as Compared to Cremophor Solubilization To determine the effect of the vesicle drug delivery systems in vivo, SCID mice with pancreatic cancer xenografts will be used. The effect of each Ceramide+delivery system alone and in combination with a chemo agent will be examined for the ability to reduce tumor size and increase survival time of the animals. A lipid fractionation study will compare the effects of C6-Ceramide as solubilized in Cremophor (CAS number 61791-12-6), a polyethoxylated castor oil mixture, to C6-Ceramide as solubilized in DPGG and PEG2PE preparations. Active agents to be evaluated include Paclitaxel, Oxaliplatin, Cisplatin, Doxorubicin, Gemcitabine, and Cetuximab.

For example, in vivo human pancreatic tumor mice xenograft model SCID/Beige/Taconic male mice will be inoculated s.c. with $2 \times 10^6$ L3.6 pancreatic cancer cells. Palpable tumors will be allowed to form over a period of 4 days. Treatments will begin on the 5th day after inoculation with thrice weekly (3×/wk) intraperitoneal (I.P.) injections of Paclitaxel (Taxol) 3.0 mg/kg or Gemcitabine (Gem) 10 mg/kg or Cetuximab 10 µg/kg, all in absence of Ceramide+delivery system. The regimen will be repeated in another set of animals that receive Ceramide+delivery system alone and then Ceramide+delivery system in combination with active agent. The Ceramide+delivery system will be delivered initially via tail vein. If that proves problematic, I.P. injections will be used.

Mice will be observed every week for 6 weeks after treatment and will be autopsied when near death. Mice survival, tumor volume (in $cm^3$), body weight (in grams) will be recorded. Average rate of tumor development will be calculated by total volume dividing by total number of days monitored. (Animal studies will be carried out under protocol approved by IACUC).

Table 3 reflects the number of mice that will be used to test the efficacy of combinations of both the three delivery methods of Ceramide C6 (Cremophor, fraction #5 and fraction #7) and their efficacy with Gemcitabine, Oxaliplatin, Paclitaxel and Cetuximab. Initially, L3.6 cells will be used, followed by similar studies using the other lines PANC and MIA as dictated by the initial study. 214 total mice are anticipated to be necessary based on 105 mice for study group A and 105 mice for study groups B and C. Drug doses will be C6-Ceramide (10 mg/kg), Paclitaxel (3.5 mg/kg), Oxaliplatin (25 mg/kg), Gemcitabine (10 mg/kg), Cetuximab (6 mg/kg).

TABLE 3

|  | Cremafore | Fraction #5 | Fraction #7 |
|---|---|---|---|
| A |  |  |  |
| Media Control | 5 | 5 | 5 |
| C6 Ceramide alone | 5 | 5 | 5 |
| Paclitaxel alone | 5 | 5 | 5 |
| Paclitaxel + C6 Ceramide | 5 | 5 | 5 |
| Cetuximab alone | 5 | 5 | 5 |
| Cetuximab + Paclitaxel | 5 | 5 | 5 |
| B |  |  |  |
| Media Control | 5 | 5 | 5 |
| C6 Ceramide alone | 5 | 5 | 5 |
| Oxaliplatin alone | 5 | 5 | 5 |
| Oxaliplatin + C6 Ceramide | 5 | 5 | 5 |
| C |  |  |  |
| Media Control | 5 | 5 | 5 |
| C6 Ceramide alone | 5 | 5 | 5 |
| Gemcitabine alone | 5 | 5 | 5 |
| Gemcitabine + C6 Ceramide | 5 | 5 | 5 |

Example 8: C6 Ceramide Potentiates Paclitaxel and Gemcitabine-Mediated Anti-Tumor Effects Against Pancreatic Cancer In Vivo and In Vitro Via Inhibition of Pro-Survival PI3k/AKT/mTOR and ERK/MAPK Pathways Materials and Methods:
 Chemicals and Reagents:
 C6 Ceramide was provided by Avanti (Alabaster, AB,CN: 860506P), Paclitaxel and Gemcitabine were obtained from the pharmacy at Roger Williams Medical Center. LY 294002, rapamycin and U0126 were purchased from CalbioChem (San Diego, Calif.). ERK1/2, AKT1/2, goat anti-rabbit IgG-HRP and goat anti-mouse IgG-HRP antibodies were purchased from Santa Cruz Biotechnology (Santa Cruz, Calif.). Monoclonal mouse anti-βactin was obtained from Sigma (St. Louis, Mo.). Antibodies to p-AKT (S473), p-AKT (T308), p-S6K (Thr389), p-4E-BP1 (S65), p-4E-BP1(T37/46), p-S6 (S235/236), p-GSKα/β (Ser21/9), p-ERK1/2 (T202/Y204) antibody were purchased from Cell Signaling Technology (Beverly, Mass.).

Cell Culture:
 Pancreatic cancer cell lines L3.6, PanC-1 and MIA-PaCa2 cells (MIA) were maintained in DMEM medium (Sigma, St. Louis, Mo.), supplemented with a 10% fetal bovine serum (Invitrogen, Carlsbad, Calif.), Penicillin/Streptomycin (1:100, Sigma, St. Louis, Mo.) and 4 mM L-glutamine (Sigma, St. Louis, Mo.), in a $CO_2$ incubator at 37° C. For Western blot analysis, cells were reseeded in 6-well plates at a density of $0.5\times10^6$ cells/mL with fresh complete culture medium.

Cell Viability Assay:
 Cell viability was measured by the 3-(4,5-dimethylthiazol-2-yl)-2,5-diphenyltetrazolium bromide (MTT) method, as described previously (Cao, C., et al. Sci Signal, 2: ra17, 2009; and Vanhaesebroeck, B., et al. Annu Rev Biochem, 70: 535-602, 2001). Briefly, the cells were collected and seeded in 96-well plate at a density of $2\times10^5$ cells/$cm^2$. Different seeding densities were optimized at the beginning of the experiments. After overnight incubation cells were exposed to fresh medium containing indicated reagents at 37° C. After incubation for different time periods, 20 µl of MTT tetrazolium (Sigma, St. Louis, Mo.) salt dissolved in Hank's balanced salt solution at a concentration of 5 mg/ml was added to each well and incubated in a $CO_2$ incubator for an additional 4 hours. The medium was subsequently aspirated from each well and 150 µl of DMSO (Sigma, St. Louis, Mo.) was added to dissolve formazan crystals and the absorbance of each well was obtained using a Dynatech MR5000 plate reader at a test wavelength of 490 nm with a reference wavelength of 630 nm.

Western Blot:
 As described before (Shrayer, D., et al. ASCO vol 24, N182, Abst 13135, 2006), aliquots of 30-40 µg of protein from each sample (treated as indicated in the Brief Description of the Figures) were separated by 10% SDS-polyacrylamide gel electrophoresis (SDS-PAGE) and transferred onto a polyvinylidene difluoride (PVDF) membrane (Millipore, Bedford, Mass.). After blocking with 10% instant nonfat dry milk for 1 hour, membranes were incubated with specific antibodies overnight at 4° C. followed by incubation with secondary antibodies (HRP-conjugated anti-rabbit or anti-mouse IgG at the appropriate dilutions) for 60 minutes at room temperature. Antibody binding was detected with the enhanced chemiluminescence (ECL) detection system (Amersham Biosciences, Piscataway, N.J.).

In Vivo Human Pancreatic Tumor Mouse Xenograft Model:
 SCID/Beige/Taconic male mice were inoculated with $2\times10^6$ L3.6 pancreatic cells and begun treatment 4 days post tumor implant with thrice weekly (3×/wk) intraperitoneal (I.P.) injections of Paclitaxel (Taxol) 3.0 mg/kg or Gemcitabine (Gem) 10 mg/kg—after treatment and were autopsied when near death (as per IRB committee). Mouse survival, tumor volume (in $cm^3$), and body weight (in grams) were recorded. Average rate of tumor development was calculated by dividing total tumor volume by total number of days monitored.

Results:
C6-Ceramide Dramatically Enhances Paclitaxel (Taxol) Induced Cell Death in L3.6 Pancreatic Cancer Cells In Vitro
 The synergism of Paclitaxel and C6-Ceramide in killing L3.6 cells in vitro was examined by MTT assay in which cell death was reflected as reduced MTT value. C6-Ceramide, which alone has limited effect on L3.6 cell viability, dramatically enhanced Paclitaxel-induced cell death in a dose dependent manner (FIGS. 4A and C). For example, 1.5 ug/ml Taxol killed 30% of cells and 10 ug/ml C6-ceramide had no effect. However, when 1.5 ug/ml Taxol was combined with 10 ug/ml C6-ceramide, there was 90% cell death. Importantly, when L3.6 cells were cultured in 10% FBS, neither Taxol or C6-Ceramide alone had any meaningful effects on L3.6 cell death, whereas combination of these two agents at a very low concentration caused significant cell death (FIGS. 4B and D): for example 2.5 µg/ml of C6-Ceramide plus 1.5 µg/ml of Taxol induced more than 70% cell death of L3.6 cells, while neither of these two alone had any measurable effect on L3.6 cell death when cultured in 10% FBS, indicating the synergism between these two.

C6-Ceramide and Taxol Induces Synergistic Anti-Tumor Effect In Vivo
 Synergistic anti-tumor effects between C6 Ceramide and Taxol were examined in vivo using the heterotransplanted L3.6 cell model in SCID mice. As shown in FIGS. 5A and B, only the group that received a combination of Taxol (3 mg/kg) and C6-Ceramide (10 mg/kg) treatment showed significantly smaller tumor volumes and enhanced survival as compared to the control treatment group and the groups that received single treatments of Taxol (3 mg/kg) or C6-Ceramide (10 mg/kg) which had minimal effects on tumor volume and mouse survival (FIGS. 5A and B). The average rate of tumor development was reduced to 0.007 cm$^3$/day in the group receiving the Taxol plus C6-Ceramide treatment compared to 0.046 cm$^3$/day in the control groups (FIG. 5D). Further, the mean survival was extended to 35.2 days in the group receiving combined therapy (Taxol/C6-ceramide) compared to 17.8 days in control and single agent treated mice (FIG. 5C). The body weight of mice that received combined treatment was actually better than the control or individual agent treatment groups indicating relative safety of this strategy (FIG. 5E).

Combinations of C6-Ceramide and Taxol, Gemcitabine, or Cetuximab Result in Synergistic Anti-Tumor Effects In Vitro The synergistic anti-tumor effect of Taxol, Gemcitabine and Cetuximab with C6-Ceramide in three different pancreatic tumor cell lines was examined in vitro. As observed for Taxol in L3.6 cells, C6-ceramide also synergized with Taxol, and Gemcitabine in enhancing cytotoxicity of 3 pancreatic cancer cell lines. None of Gemcitabine (3 µg/ml), Taxol (15 ug/ml) or C6-Ceramide (10 ug/ml) alone had a significant effect in inducing cell death whereas combination of either chemo agent with C6-Ceramide caused a dramatic increase in cell death in pancreatic cancer cell lines L3.6 (6A), Panc-1 (6B), and MIA cells (6C). Of added importance are results observed with the combination of C6-ceramide and Cetuximab. In the three cell lines examined, neither agent alone had significant cytotoxic effect. However combining the two agents induced >50% cell death in contrast to the lack of effect by Cetuximab alone (FIG. 6A, B, C). This is an unexpected result as Cetuximab, an EGFR inhibitor, is normally inactive against KRAS mutant cancers, (suggesting a bypass or nullifying effect by C6 Ceramide on the inhibiting KRAS effect.

Figure 7:
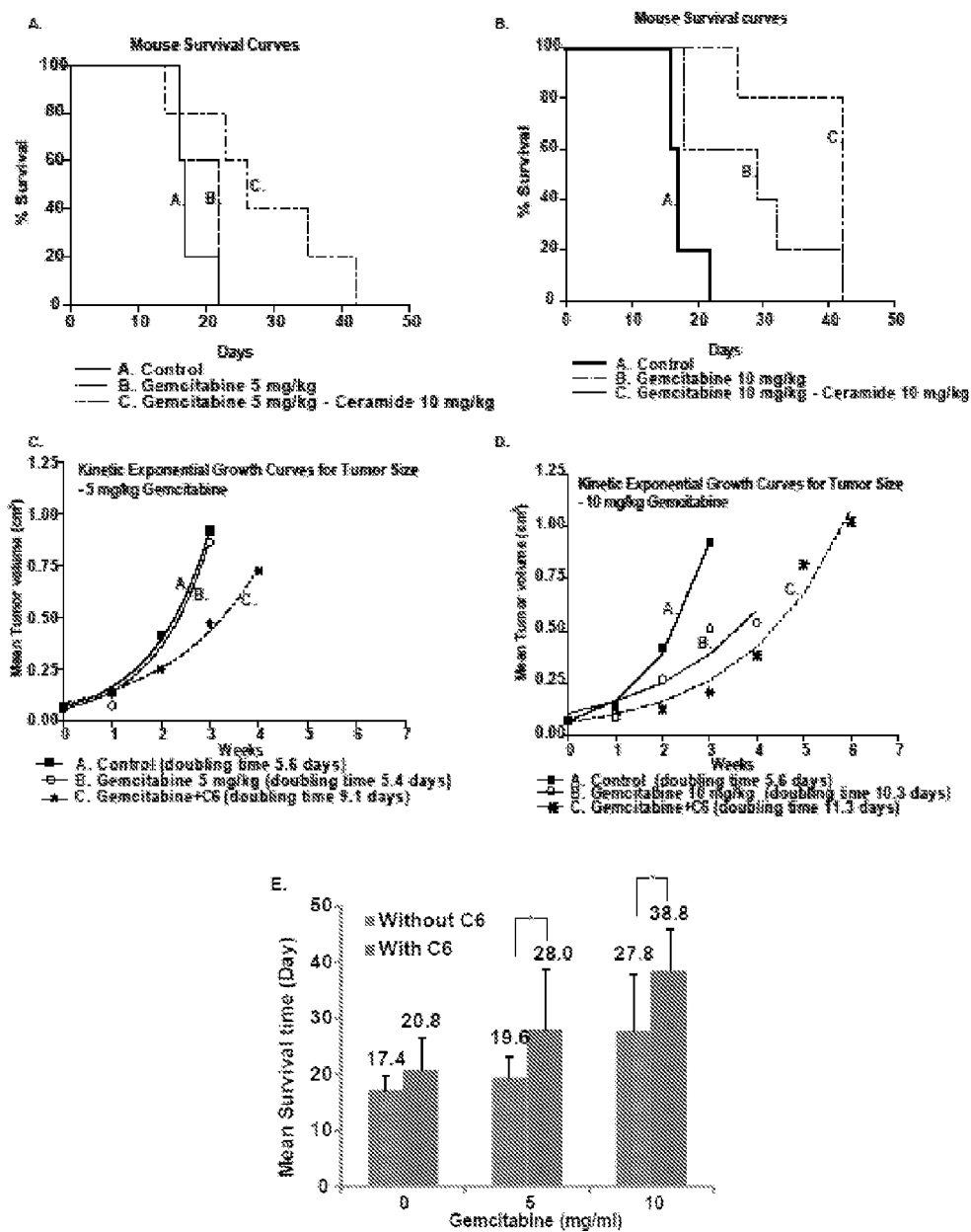
FIG. 7 depicts data showing synergistic anti-tumor effects of C6 Ceramide and Gemcitabine in vivo.

A Combination of C6-Ceramide and Gemcitabine Results in Synergistic Anti-Tumor Effects In Vivo The combination effect of C6-ceramide on Gemcitabine-induced tumor regression in vivo in the L3.6 pancreatic cancer cell were examined using same methods as discussed above for Taxol. As shown in FIG. 7A-D, low dose Gemcitabine treatment (5 mg/kg) and intermediate dose gemcitabine treatment (10 mg/kg) had limited effect on survival and tumor growth, demonstrating only a moderate anti-tumor effect in the L3.6 cell SCID mice tumor model. Combining Gemcitabine with C6-ceramide (10 mg/kg), however, resulted in a marked anti-tumor effect, indicated by significant tumor regression (FIG. 7C, 7D) with overall reduced tumor size and significant prolongation of survival time in the mice that received both C6-ceramide and Gemcitabine treatment (FIG. 7E).

Combination of C6-Ceramide with Gemcitabine or Taxol Synergistically Inactivates Multiple Pro-Survival Signaling Pathways The effects of these synergisms on the pro-survival AKT/mTORC1 signaling axis and KRAS/MEK/ERK activation axis, two major cancer promoting survival pathways (FIG. 8), were investigated. Levels of phospho-AKT and phospho-GSK-3-a/b were assessed as measures of the AKT activity. Phospho-p70 S6 kinase, phospho-S6 ribosomal protein, and phospho-4E-BP1 were used as measures of mTORC1 activity downstream of AKT. Levels of phospho-ERK 1/2 were measured as downstream indicators for KRAS activity.

As shown in FIG. 8A, Gemcitabine itself had no effect on AKT/mTORC1 or ERK activation in the 2-6 h time period examined. C6-Ceramide induced moderate inhibition of AKT/mTORC1 and ERK activation. A combination of Gemcitabine and C6-Ceramide, however, caused a profound inhibition of both AKT/mTORC1 and ERK signaling (FIGS. 8A and B). Quantitation of Gemcitabine effects at 4 h is shown in FIG. 8B. AKT/mTORC1 and ERK signaling were also strongly inhibited by combination treatment of Taxol plus C6-ceramide (FIGS. 8C and D). Quantitation of Taxol effects at 4 h is shown in FIG. 8D.

The data suggest that combining C6-Ceramide with Gemcitabine or Taxol causes inactivation of AKT/mTORC1 and ERK in vitro, which might be the key mechanism to explain the synergisms (FIG. 8B, 8D). To further explore this notion, various inhibitors of AKT/mTORC1 or ERK signaling pathways were used to assess possible involvement of these pathways by assessing whether they might substitute for C6-ceramide. A PI3K/AKT inhibitor (LY 294002), mTORC1 inhibitor (rapamycin), MEK/ERK inhibitor (U0126) were utilized for these studies. The data are shown in FIGS. 9A and B.

LY294002, rapamycin, U0126, Taxol, or Gemcitabine alone had little or no significant effect on L3.6 cell viability. However, combination of Taxol or Gemcitabine with either inhibitor resulted in marked inhibition of cell viability (FIG. 9A). Notably, the greatest loss of cell viability was observed when either Taxol or Gemcitabine was combined with LY29002+U0126, indicating that greatest synergism is observed when both the Akt and ERK pathways are simultaneously inhibited (FIG. 9A). This was also reflected in effects on levels of p-AKT, p-S6/p-4E-BP1, and p-ERK, where Gemcitabine alone had little effect while the combination with the respective inhibitor resulted in marked decrease in the levels of the target phosphoprotein (FIG. 9B).

Thus Inhibitors of PI3K/Akt (LY294002), mTORC1 (rapamycin), and MEK/ERK (U0126) mimicked the effect of C6-ceramide on L3.6 cell viability when combined with either Taxol or Gemcitabine. These data suggest that chronic activation of the PI3K/AKT/mTORC1 and MEK/ERK signaling pathways may be a major cause of pancreatic cancer cell chemo-resistance to Gemcitabine, Taxol, and Cetuximab. C6-Ceramide appears to reverse the activation of these pathways, thus potentiating the cytotoxic effects of the chemotherapeutic agents on the pancreatic cancer cells. Thus C6-Ceramide may shut down the "running motor which energizes the chemo-resistance" in the cancer cell.

Discussion

Figure 4:
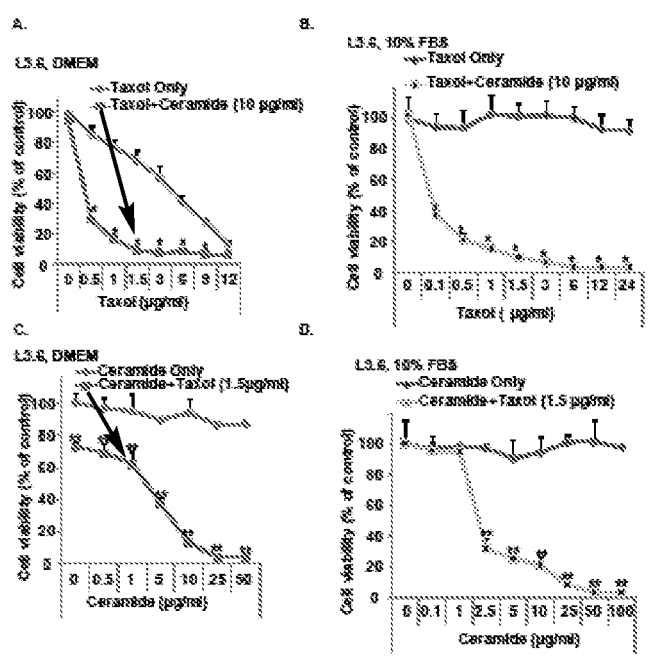
FIG. 4 depicts data showing that C6-Ceramide dramatically enhances Taxol-induced cell death in L3.6 pancreatic cancer cells in vitro. L3.6 pancreatic cancer cells, cultured either in basic DMEM medium or with 10% FBS, were treated with indicated doses of Taxol in the presence or absence of C6 Ceramide (10 μg/ml) for 48 hours, cell viability was detected by MTT assay (FIGS. 4A and B). L3.6 cells, cultured either in basic DMEM medium or with 10% FBS, were treated with indicated dose of C6 Ceramide in the presence or absence of Taxol (1.5 μg/ml) for 48 hours, cell viability was detected by MTT assay as described (FIGS. 4C and D). Mitomycin C (10 μg/ml) was always present in the media to prevent cell proliferation from occurring. The data represent the mean±SD of at least triplicate experiments. *P<0.05 versus group without C6 Ceramide presents (FIGS. 4A and B). **P<0.05 versus group without Taxol presents (C and D). Combination of Taxol and Ceramide induced significant cytotoxicity in DMEM or 10% FBS media.
Figure 5:
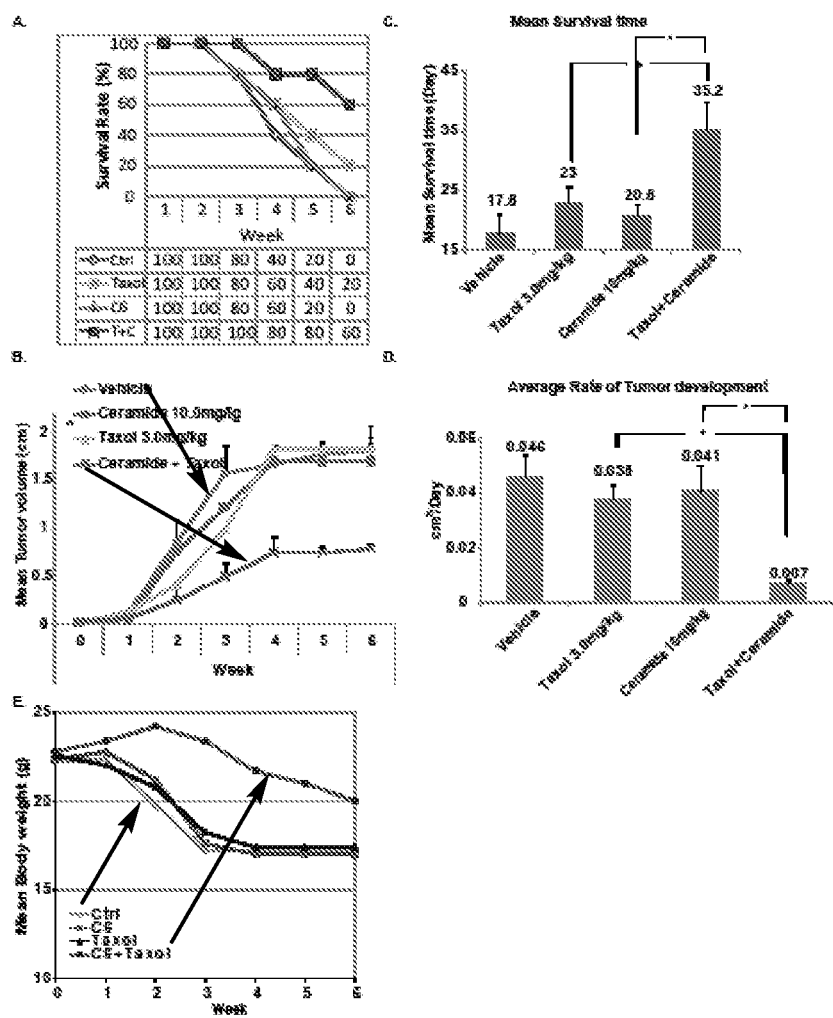
FIG. 5 depicts data showing that C6 Ceramide and Paclitaxel cause synergistic anti-tumor effects in vivo. SCID/Beige/Taconic nude male mice, 22-25 g, 6-8 weeks old were ear tagged and randomized into 4 different groups (Control, Ceramide, Paclitaxel, Ceramide+Paclitaxel) of 5 mice each prior to inoculation s.c. with $2\times10^6$ L3.6 cells in a volume 0.1 ml into the internal surface of the right thigh. Treatment was started 4 days after L3.6 cell injection with thrice weekly (3×/wk) intraperitoneal (I.P.) injections of Paclitaxel 3.0 mg/kg with or without C6-Ceramide (10 mg/kg) for 2 weeks. Mice survival (A and C), tumor volume (in $cm^3$) (B), mice body weight (in grams) were recorded (E). Average rate of tumor development was calculated by total tumor volume dividing by total number of days monitored (D). The experiments in this figure were repeated at least three times and similar results were observed. Combination Taxol with Ceramide was associated with significant tumor regression, and increased survival with maintenance of body weights.
Figure 6:
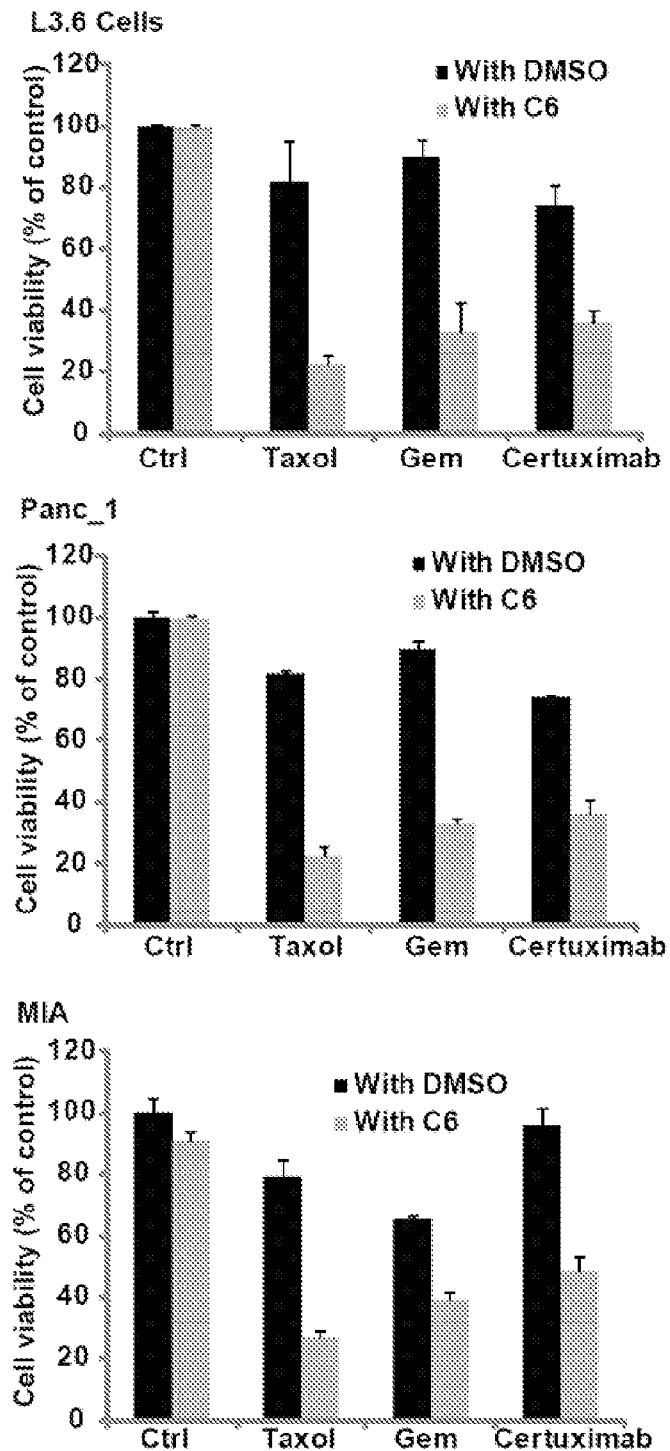
FIG. 6 depicts data showing synergistic effects of C6-Ceramide to potentiate the cytotoxicity of Paclitaxel (Taxol), Gemcitabine, and Cetuximab in L3.6, Panc-1, and MIA PaCa2 pancreatic cancer cell lines. Pancreatic cancer cell lines including L3.6 cells, Panc-1, and MIA-PaCa2 (MIA), cultured in basic DMEM medium, were treated with Taxol (3 ug/ml), Gemcitabine (3 ug/ml), or Cetuximab (10 ug/ml). Mitomycin C (10 ug/ml) was always present in the media to prevent cell proliferation from occurring. The data represent the mean±SD of at least triplicate experiments. *P<0.05 versus group without C6 Ceramide present. The experiments in this figure were repeated at least three times and similar results were observed. Combination of C6-Ceramide with oncologic drugs (Taxol, Gemcitabine, or Cetuximab) was associated with significant increased cytoxicity vs. chemo drug alone.

This Example has demonstrated that co-administration C6-Ceramide and clinically relevant chemotherapy agents (Gemcitabine or Taxol) caused a synergistic anti-tumor effect both in 3 different cultured pancreatic cancer cell lines and in the L3.6 pancreatic cancer SCID mice model (FIG. 4, FIG. 5, and FIG. 6). Analysis of molecular mechanisms strongly suggests that exogenous cell permeable C6-Ceramide inactivates both the pro-survival and KRAS (mutant) pathways responsible for chemo resistance to Paclitaxel and Gemcitabine. The anti-tumor response and post treatment survival exhibited a similar pattern. The anti-tumor response and the post treatment survival with singular treatment chemo agents (Gemcitabine, Paclitaxel, Cisplatin, Oxaliplatin and C6 Ceramide) alone were similar to the anti-tumor response and survival in control mice. Only combined therapy with C6 Ceramide and the selected agent induced a significant increase in tumor regression and significant prolongation of survival.

Figure 9:
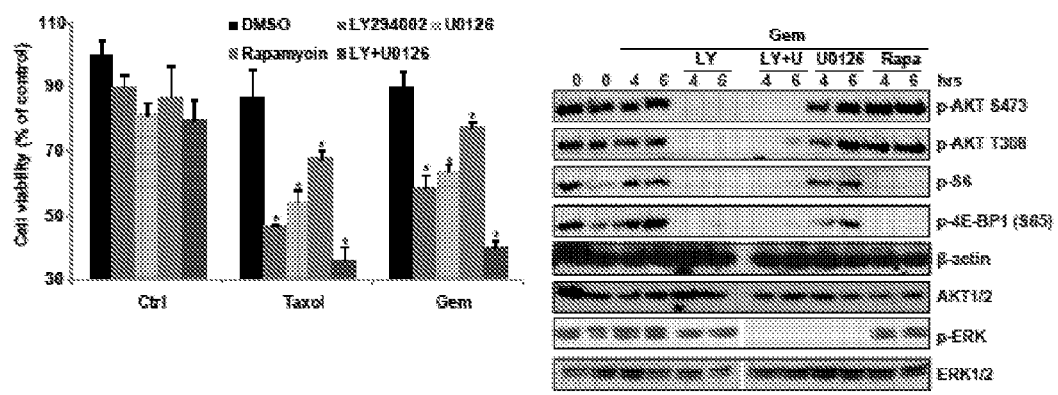
FIG. 9 depicts data showing the effect of survival pathway inhibitors on cytotoxicity of Taxol and Gemcitabine in L3.6 pancreatic tumor cells. L3.6 cells were pretreated with various inhibitors including PI3K/AKT inhibitor LY 294002 (LY, 1 μM), mTORC1 inhibitor rapamycin (100 nM), MEK/ERK inhibitor U0126 (1 μg/ml), alone or in the presence of Taxol (1.5 μg/ml) or Gemcitabine (1 μg/ml) for 48 hours, with cell death detected 48 hours later (FIG. 9, left). Effects of various inhibitors as mentioned above on AKT/mTORC1 and ERK activation were also examined by Western blots using commercially available antibodies (FIG. 9, right). *P<0.05 versus group without C6 Ceramide presents. The experiments in this figure were repeated at least three times and similar results were observed. At the doses used, the inhibitors had no significant effect on cell viability. However in combination with a subtoxic concentration of Taxol or Gemcitabine, all of the inhibitors produced significant loss of cell viability. Gemcitabine alone had little effect on components of the PI3K/Akt/mTORC1 and MEK/ERK signaling pathways. However, the combination of Gemcitabine with the respective inhibitors produced a marked inhibition of the respective target phosphoprotein. The combination of LY and U0126 with Gemcitabine inhibited all of the target phosphoproteins at 4 and 6 hours.

An explanation of the molecular framework of the pro-survival pathway suggests the activation of phosphoinositide-dependent kinase-1 (PDK1) and recruitment of the serine/threonine kinase AKT to the plasma membrane involving PI3K and leading to phosphorylation of AKT at Thr308. This phosphorylation is sufficient for AKT activation, but for a maximal AKT activity an additional phosphorylation of the Ser473 residue is required. It is now well established that the mTOR complex 2 (mTORC2), a complex composed of mTOR, SIN1, mLST8 and rictor, is the upstream kinase complex for AKT phosphorylation at Ser 473. Besides the growth promoting potential of AKT, its anti-apoptotic properties are closely linked to the resistance of cancer cells to a broad spectrum of apoptotic stimuli. Multiple groups have reported that activation of the P13K/AKT signaling is the major cause of resistance by the pancreatic cancer cell against Gemcitabine induced cell death. In contrast, inhibition of PI3K/AKT enhances Gemcitabine induced apoptosis in human pancreatic cancer cells both in vivo and in vitro. It is also well established that inhibition of PI3K/AKT pathway enhances Paclitaxel induced cancer cell death. The mechanisms by which AKT promotes cell survival under treatment with cytotoxic drugs include phosphorylation and thereby inactivation of pro-apoptotic proteins such as BAD, caspase-9 and members of the Forkhead family of transcription factors. Activation of PP2A and its family members by cell-permeable Ceramide results in dephosphorylation and inhibition of AKT and is involved in Ceramide-induced apoptosis. Recent studies also indicate that protein kinase Czeta may also be involved in Ceramide-induced AKT inhibition. Ceramide was shown to induce complex formation between PKCzeta and Akt which may block Akt phosphorylation. As described in this Example, activation of PI3K/AKT/mTOR pathway is important for the resistance against Gemcitabine- and Paclitaxel-induced pancreatic cancer cell death, since each individual inhibitor of PI3K/Akt (LY294002) and mTOR (rapamycin) largely sensitized L3.6 pancreatic cancer cells to Gemcitabine- and Paclitaxel-induced cell death (FIG. 9). It addition, this Example describes that adding exogenous cell permeable C6 Ceramide caused AKT and downstream mTORC1 inactivation. Also of interest, Paclitaxel or Gemcitabine, which by themselves had no effect on PI3K/AKT activation, dramatically enhanced C6-Ceramide induced AKT dephosphorylation or inhibition.

Figure 8:
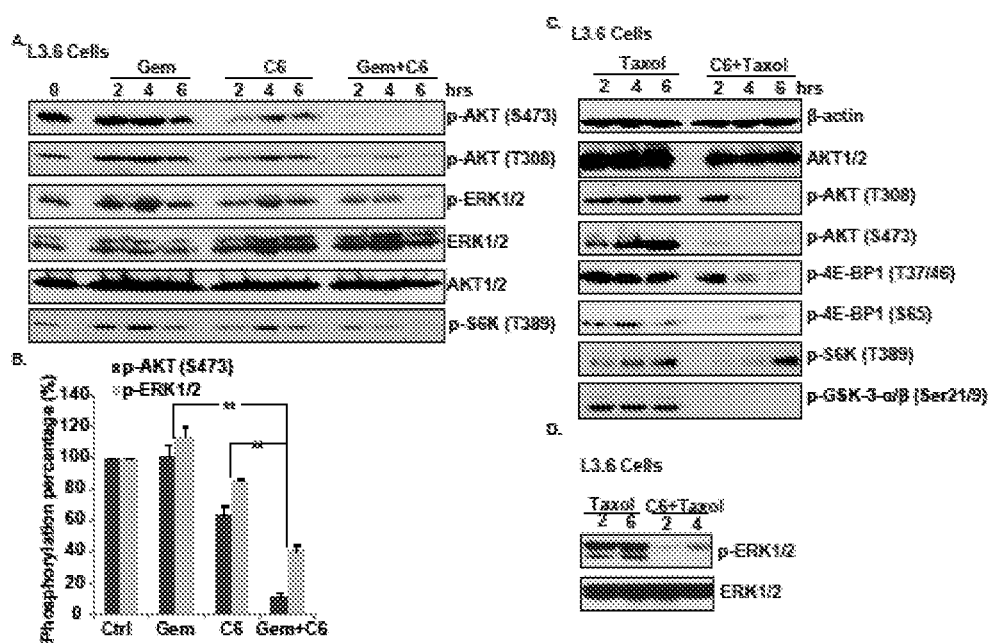
FIG. 8 depicts data showing that C6 Ceramide plus Gemcitabine or Taxol causes inactivation of AKT/mTORC1 and ERK in vitro. Pancreatic cancer cell line L3.6 cells were left untreated or treated with Gemcitabine (Gem, 1 μg/ml) or Taxol (1.5 μg/ml) in the presence or absence of C6 Ceramide (10 μg/ml) for 2, 4, and 6 hours, AKT/mTORC1 and ERK activation were detected by Western Blot using the indicated antibodies (FIGS. 8A and 8B and FIGS. 8C and 8D). p-AKT (S473) and p-ERK at 4 hour time intervals for each treatment are quantified in FIGS. 8B and 8D. C6 Ceramide combined with Gemcitabine or Taxol induced significant inhibition of AKT/mTORC-1 and ERK activation at 4 and 6 hours, compared to either compound alone.

This Example described that PI3K/AKT/mTORC1 is not the only signal pathway that is affected by exogenous cell permeable C6 Ceramide treatment. ERK MAPK signaling is also inhibited by C6 Ceramide treatment at least in L3.6 pancreatic cancer cells, and thus adding Paclitaxel or Gemcitabine enhanced its inhibition of ERK activation (FIG. 8). In L3.6 cells, it seems that ERK activation is a chemoresistance factor, since U0126, a well characterized MEK/ERK inhibitor, sensitized L3.6 cells to Gemcitabine- and Paclitaxel-induced cell death (FIG. 9A). Furthermore, the PI3K/Akt pathway and MEK ERK pathway interact in concert since, the combination of the two inhibitors LY294002 and U0126 had little effect on cell viability, but gave the greatest decrease in cell viability when the pair was combined with subtoxic doses of either Taxol or Gemcitabine (FIG. 9A). Although biochemical mechanisms underlying the ERK MAPK inhibition effect of Ceramide have not been thoroughly characterized in this study, some direct targets of Ceramide might be involved, which deserves further investigation.

Of note is the ability of C6 Ceramide to enhance the cytotoxicity of Cetuximab in three different pancreatic cancer cell lines, as shown in FIG. 6. This was highly unexpected, as pancreatic cancer is commonly KRAS mutated and does not respond to Cetuximab (an EGFR inhibitor) since constitutive activation occurs downstream of growth factor binding. Furthermore, hepatic colorectal cancer metastases of KRAS mutant tumors are insensitive to Cetuximab, in contrast to the high responsiveness to Cetuximab plus chemotherapy in KRAS wild type tumors.

In conclusion, in vitro findings along with in vivo results prove that C6 Ceramide is a synergistic adjuvant to conventional chemotherapeutics (Gemcitabine) for treatment of human pancreatic cancer. C6 Ceramide also potentiated the anti-tumor effect of the anti-EGFR monoclonal antibody Cetuximab, producing levels of cytotoxicity similar to that induced by Taxol and Gemcitabine.

Example 9: Paclitaxel Disrupts Polarized Entry of Membrane-Permeable C6 Ceramide into Ovarian Cancer Cells Resulting in Synchronous Induction of Cell Death Introduction The function of ceramide in apoptosis and its association with receptor-associated apoptotic signaling proteins remain unresolved. It has previously been shown that TNF-α-induced apoptosis is preceded by an increase in intracellular ceramide levels. TNF-α and exogenous C6 ceramide interfere with the activation of Raf-1 and ERK by EGF and down-regulate v-Src-induced Raf-1 kinase activity. Exogenous C6 ceramide induces endocytic vesicle formation and results in enlarged late endosomes and lysosomes in mouse fibro-blasts.

Chemotherapeutic agents, including paclitaxel and taxol, as well as physiological stimuli, such as TNF-α, stimulate ceramide accumulation and increase oxidative stress in cancer cells, and the upregulation of glucosylceramide synthase has been hypothesized to contribute to chemoresistance. Notably, multidrug-resistant cancer cells exhibit elevated levels of glucosylceramide. Agents that block ceramide glycosylation potentiate the cellular sensitivity to ceramide and chemotherapeutic agents, indicating that the ceramide metabolic pathway is an important target for anticancer drug development.

Paclitaxel has emerged as a valuable antimitotic chemotherapy drug, particularly in breast and ovarian cancer. Although cytotoxic mechanisms are well understood, the efficacy of this drug cannot be explained by microtubular interactions only. Paclitaxel-induced apoptosis has been shown to be attributable, in part, to ceramide and sphingoid bases, and the simultaneous treatment of Jurkat cells with paclitaxel and ceramide has been demonstrated to enhance paclitaxel-induced cell growth inhibition.

Paclitaxel and ceramide synergistically induce pancreatic cancer cell death through differential modulation of EGFR-mediated MAP kinases. EGFR and ERK inhibitors may further enhance the effect of paclitaxel and ceramide. The combination of paclitaxel and ceramide in biodegradable polymeric nanoparticles has been identified as an extremely effective therapeutic strategy to overcome drug resistance in ovarian cancer.

Additional studies have identified a ceramide transport protein, COL4A3BP or CERT, which sensitizes cancer cells to multiple cytotoxic agents when downregulated. COL4A3BP expression is increased in drug-resistant cell lines and in residual tumor cells following paclitaxel treatment of ovarian cancer, indicating that it may be a target for chemotherapy-resistant cancers.

Considering the rising functions of ceramide in combinatorial therapies with other chemotherapeutic agents, and the involvement of its modified form in chemoresistance, the entry of exogenous C6 ceramide was analyzed in the present Example using fluorescently-labeled C6-NBD. C6 ceramide was observed to enter the ovarian cancer cells in a polarized fashion. In addition to this, paclitaxel was observed to induce vesicle formation and prevent the polarized entry of C6 into the cancer cells, thus exhibiting a synergistic effect on apoptosis.

Materials and Methods

Chemicals and Reagents.

C6-NBD-ceramide was a gift from Avanti Polar Lipids, Inc. (Alabaster, Ala., USA). Filipin, taxol and doxorubicin were obtained from Sigma-Aldrich (St. Louis, Mo., USA). Hoechst 33342 was purchased from Molecular Probes (Calsbad, Calif., USA).

Cell Culture.

Human ovarian cancer cells (CaOV3 cells) were maintained as described previously (Qiu L, et al. Oncol Rep 16: 907-913, 2006) in DMEM (Sigma-Aldrich) supplemented with 10% fetal bovine serum, penicillin/streptomycin (1:100, Sigma-Aldrich) and 4 mM L-glutamine, in a $CO_2$ incubator at 37° C.

Confocal Microscopy.

The cells were plated in eight-well chamber slides (Lab-Tek; Nalge Nunc International, Naperville, Ill., USA) and treated with various reagents, including C6-NBD ceramide, taxol and CuSO4. Next, the cells were either left untreated or were fixed for 20 min in fresh 4% paraformaldehyde-PBS. The cell nuclei were also stained with Hoechst (1 µg/ml in PBS) for 10 min. The slides were mounted with anti-fade (Life Technologies, Grand Island, N.Y., USA) and stored in the dark until viewing. The samples were observed under a confocal microscope and images were captured by Zen 2009 Light Edition (Carl Zeiss AG, Oberkochen, Germany).

Results and Discussion

C6 Ceramide Enters Cells in a Polarized Manner.

Figure 10:
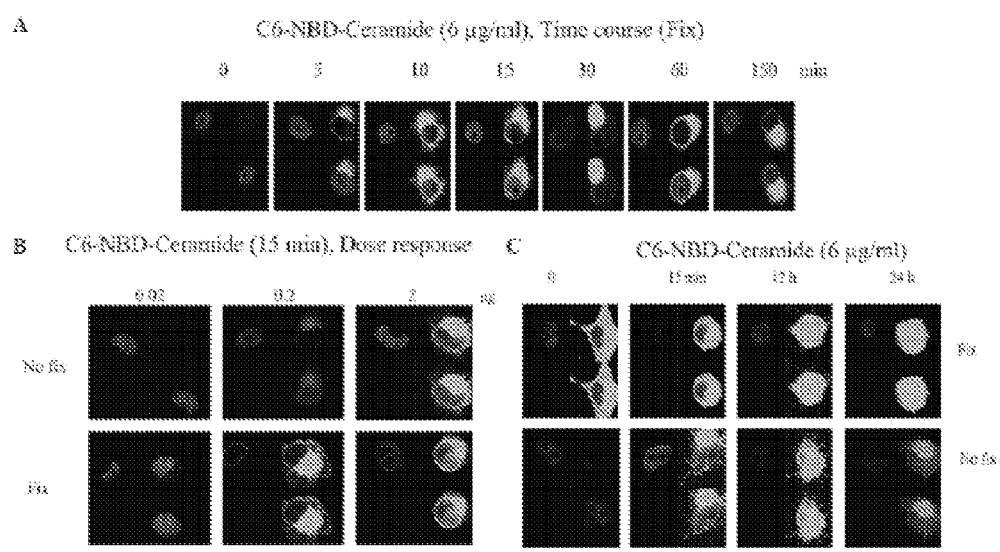
FIG. 10 depicts the polarized distribution of C6-NBD ceramide in ovarian cancer cells. (A and C) CaOV3 cells were cultured in 8-well chamber slides and treated with C6-NBD ceramide (6 μg/ml). (B) The cells were fixed with formaldehyde at various times following treatment or were treated with the indicated doses of C6-NBD-ceramide, with or without fixation. The cells were processed and observed under a confocal microscope.

The use of a combination of several chemotherapeutic agents is well accepted clinically, as it enables drugs to be administered at relatively low doses with an improved efficacy. C6 ceramide functions synergistically with taxol to inhibit cell proliferation and cell migration in cultured ovarian cancer cells. However, the molecular mechanism of this synergism remains unknown, and the entry of membrane-permeable C6 ceramide into the cells remains uncharacterized. To investigate the pattern of C6 entry into the cells, fluorescently-labeled C6-NBD was used. Ovarian cancer cells were treated with C6 ceramide and the resultant fluorescence signal was observed with or without fixation. The results indicated that C6 ceramide enters the cells in a time-(FIG. 10A) and dose-dependent (FIG. 10B) manner. Notably, the distribution of the fluorescence signal showed a polarized pattern (FIGS. 10A and B). Subsequent to 12 h, the fluorescence signal had saturated the cells (FIG. 10C).

Effect of Inhibitors of Lipid Rafts/Caveolae on C6 Ceramide Entry into Ovarian Cancer Cells.

Figure 11:
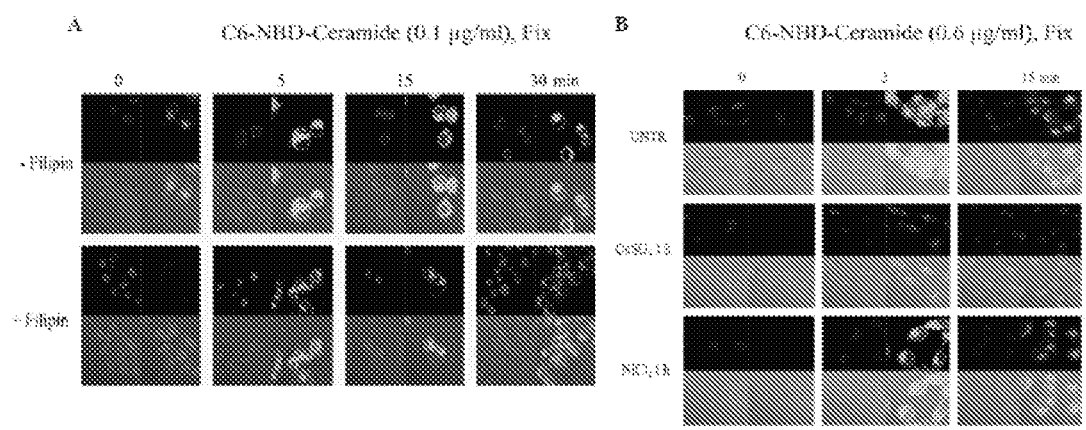
FIG. 11 depicts the effect of inhibitors on polarized entry of C6-NBD-ceramide into ovarian cancer cells. CaOV3 cells were cultured in 8-well chamber slides and treated with or without (A) a lipid raft/caveolae inhibitor or with (B) water channel inhibitors, CuSO$_4$ or NiCl$_2$. The cells were fixed with formaldehyde, processed and observed under a confocal microscope.

The data demonstrated that C6 ceramide rapidly enters cells in a polarized manner. Lipid rafts/caveolae have previously been identified as important for the process of signal transduction. To further investigate the entry of C6 ceramide, in the present study, the cells were pretreated with filipin, an inhibitor of lipid rafts/caveolae. Filipin inhibited the C6 ceramide entry into the CaOV3 cells (FIG. 11), indicating that lipid rafts/caveolae may be involved in the entry of C6 ceramide into the cells. Maintaining membrane structure or topology may potentiate the synergistic effect of taxol and ceramide on the apoptosis of cancer cells.

Effect of Water Channel Inhibitors on Entry of C6 Ceramide into Ovarian Cancer Cells.

Previous studies have demonstrated that molecules other than water may also enter the cells via water channels or aquaporins. Aquaporins also play critical roles in processes other than the transport of water. To investigate whether C6 ceramide enters the cells via aquaporins or whether the entry is only partially associated with aquaporins, the inhibitors of aquaporins, $CuSO_4$ and $NiCl_2$, were utilized. The results revealed that $CuSO_4$ inhibits C6 ceramide entry into the cells, but that $NiCl_2$ does not (FIG. 11B), indicating that C6 ceramide may partially enter the cells via aquaporins.

Effect of Taxol and Doxorubicin on the Polarized Entry of C6 Ceramide into Ovarian Cancer Cells.

Figure 12:
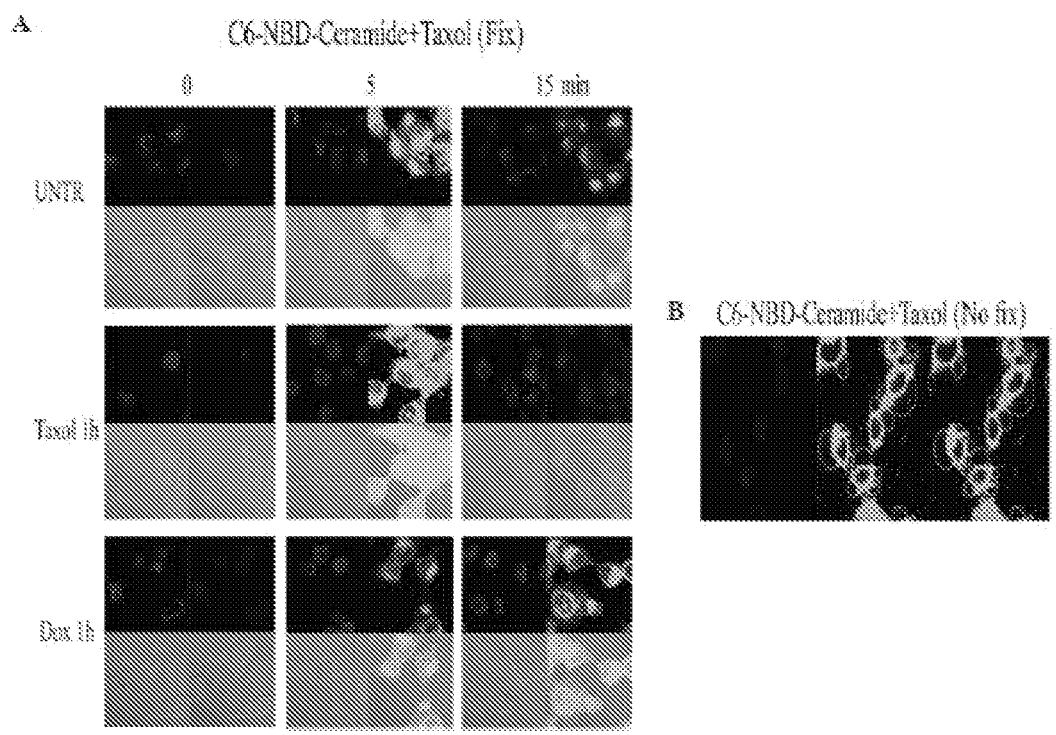
FIG. 12 depicts the effect of chemotherapeutic agents on C6-NBD-ceramide polarized entry into ovarian cancer cells. (A) CaOV3 cells were cultured in 8-well chamber slides, pretreated with taxol or doxorubicin for 1 h and then treated with C6-NBD-ceramide for 5 or 15 min. The cells were fixed with formaldehyde and processed for confocal microscopy. (B) The cells were pretreated with taxol and then C6-NBD-ceramide and processed for confocal microscopy without fixation.
Figure 13:
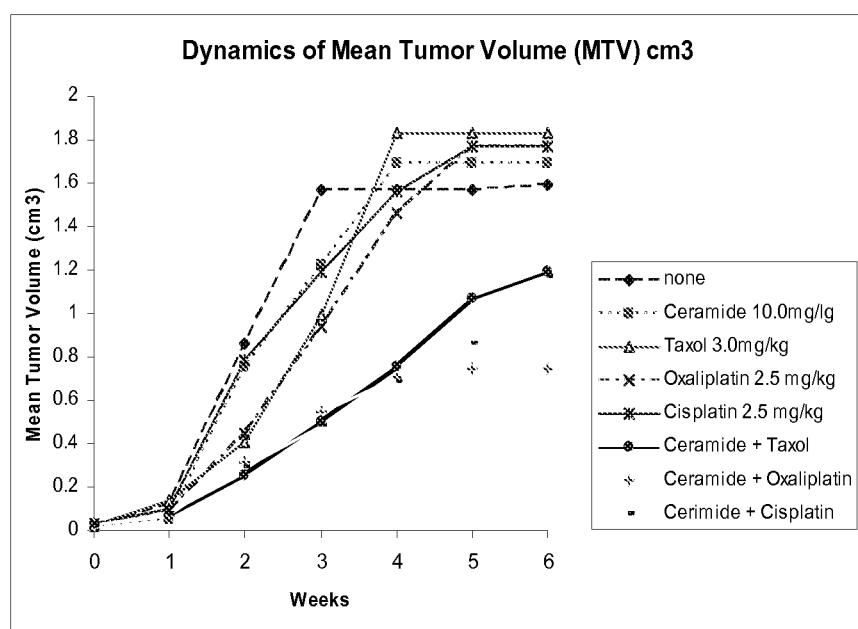
FIG. 13 depicts dose-response curves following treatment with chemotherapy regarding tumor growth.
Figure 14:
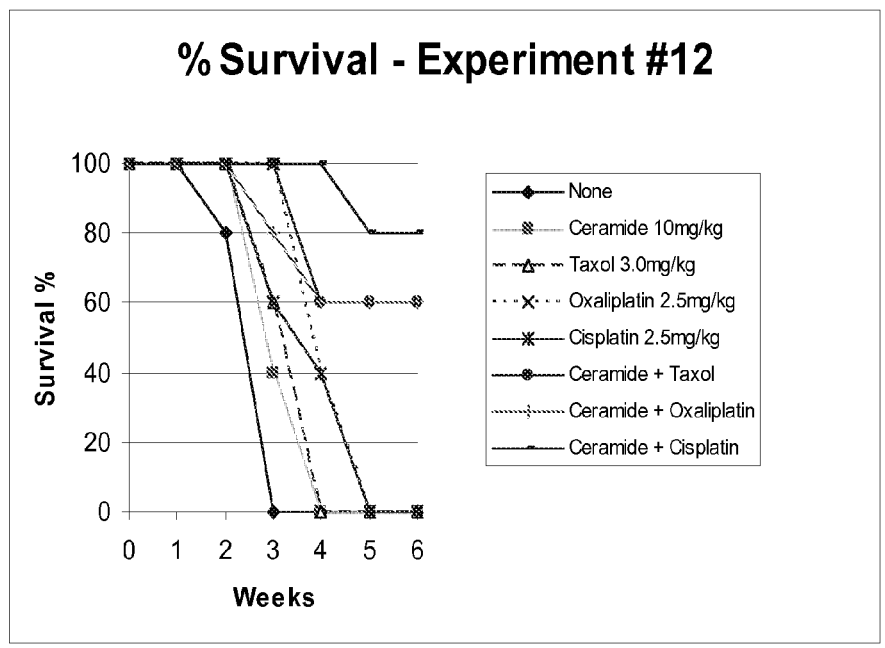
FIG. 14 depicts dose-response curves following treatment with chemotherapy regarding survival.
Figure 15:
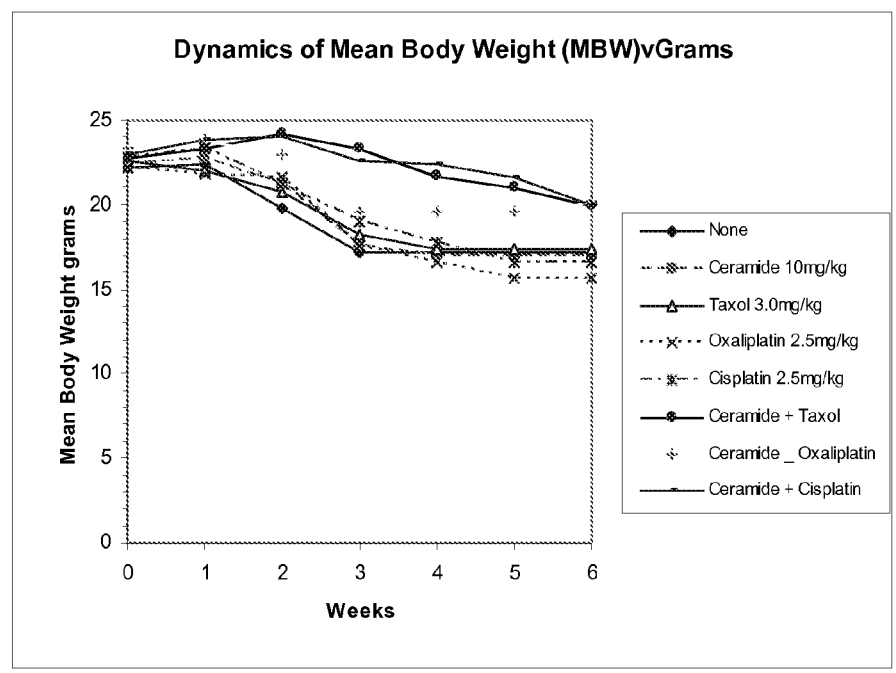
FIG. 15 depicts dose-response curves following treatment with chemotherapy regarding dynamics of body weight.
Figure 16:
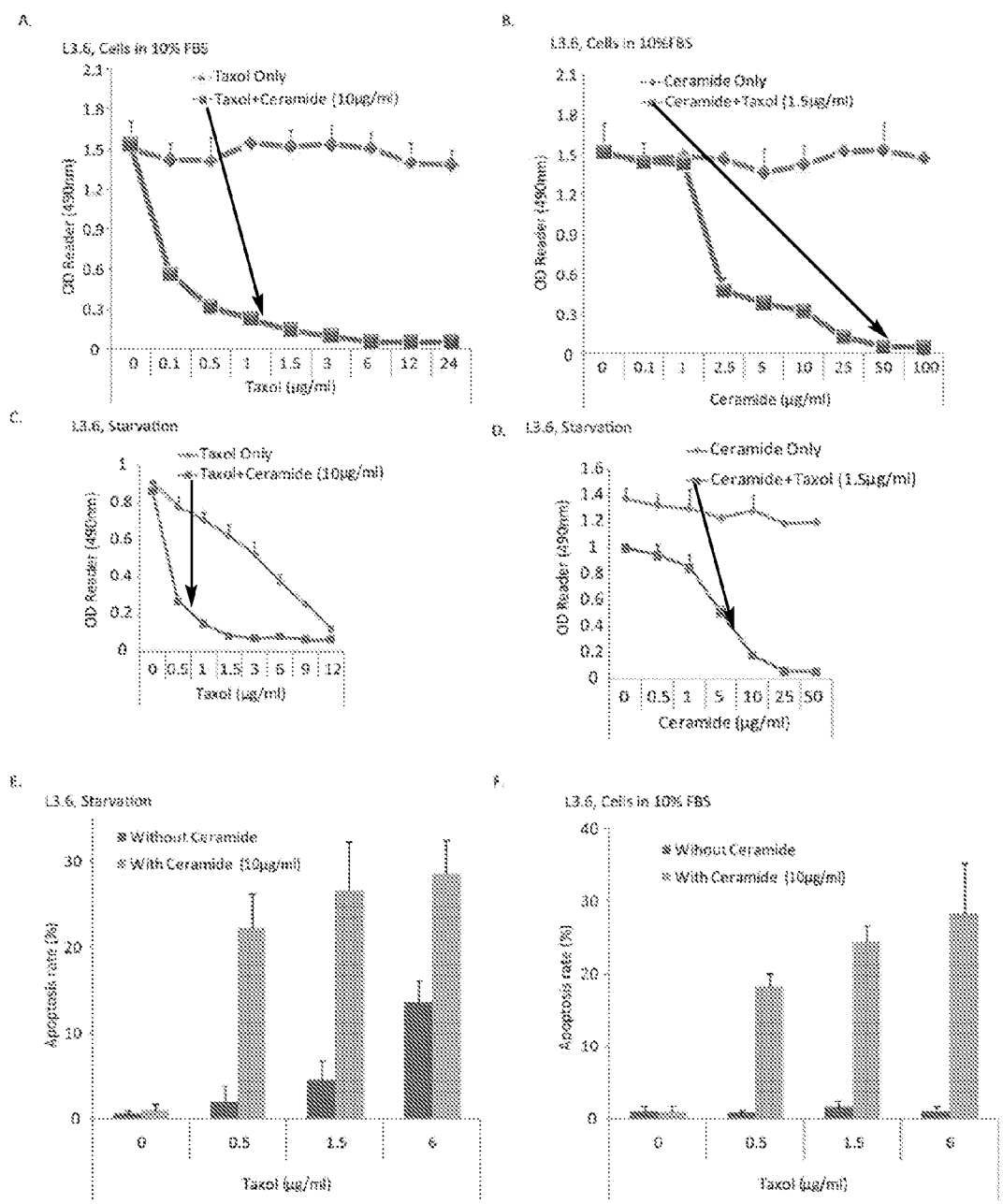
FIG. 16 depicts chemo-sensitization by C6 ceramide of pancreatic cancer cells followed by co-incubation with Taxol. (A) 10 ug/mL ceramide, cells in 10% FBS; (B) 1.5 ug/mL ceramide, cells in 10% FBC; (C) 10 ug/mL ceramide, starvation; (D) 1.5 ug/mL ceramide, starvation; (E) % apoptosis rate, with 10 ug/mL ceramide (right bar) and without ceramide (left bar), starvation; (F) % apoptosis rate, with 10 ug/mL ceramide (right bar) and without ceramide (left bar), cells in 10% FBS.
Figure 17:
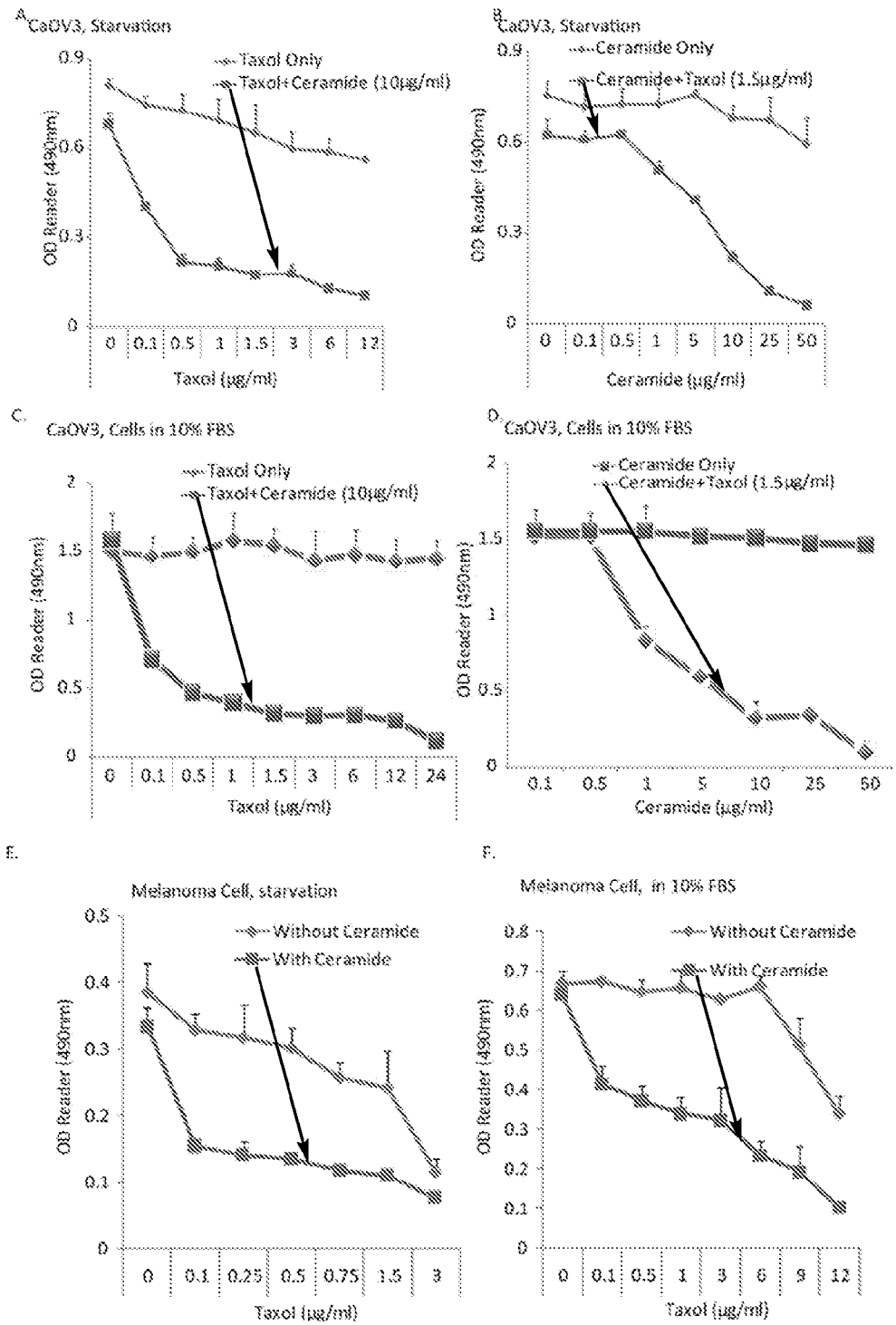
FIG. 17 depicts chemo-sensitization by C6 ceramide of ovarian cancer cells (A-D) or melanoma cells (115 cells) (E and F) followed by co-incubation with Taxol. (A) 10 ug/mL ceramide, starvation; (B) 1.5 ug/mL ceramide, starvation; (C) 10 ug/mL ceramide, cells in 10% FBS; (D) 1.5 ug/mL ceramide, cells in 10% FBS; (E) starvation; (F) cells in 10% FBS.
Figure 18:
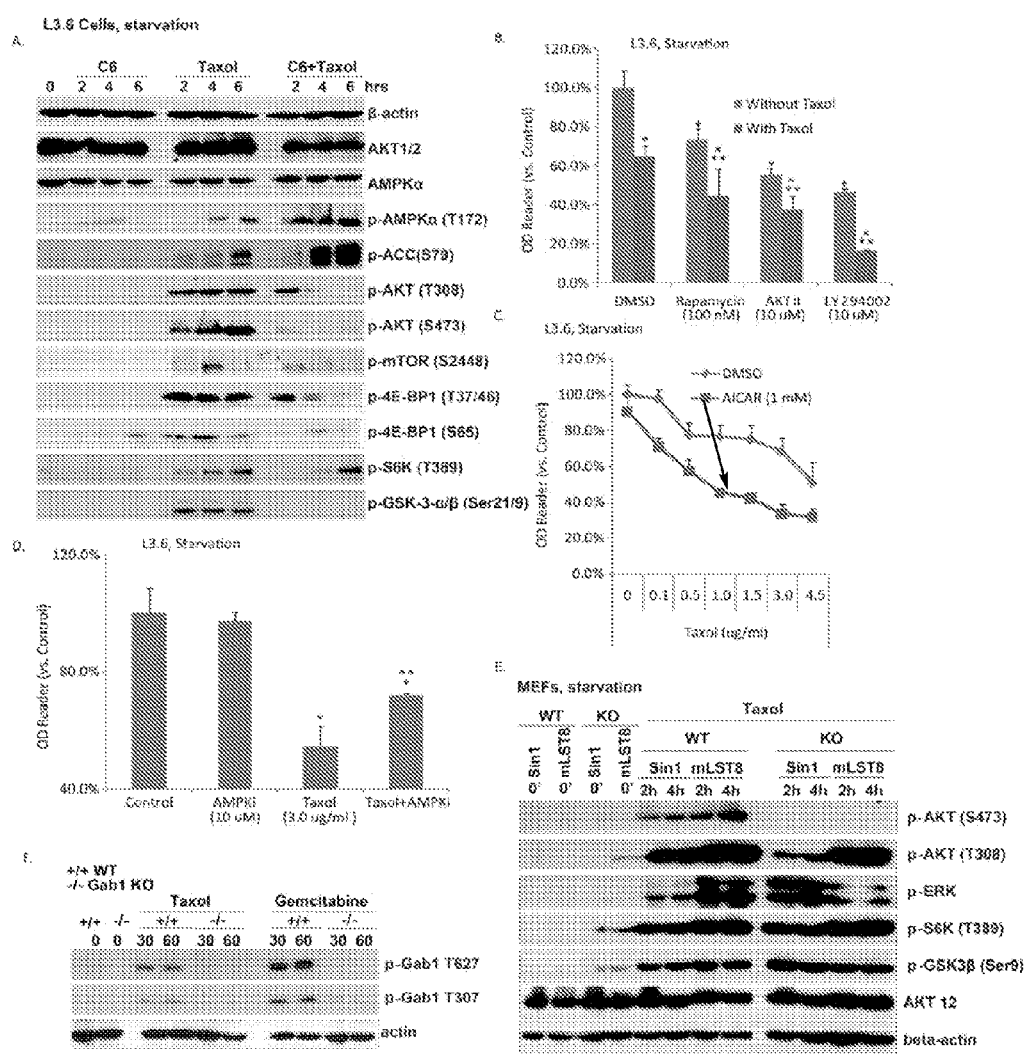
FIG. 18 depicts data summarizing the inhibition of Taxol-induced AKT/mTOR activation by C6 ceramide pre-treatment (0.5 h), while leaving AMPK activation dramatically enhanced. In (B), left bar=without Taxol, and right bar=with Taxol.

Paclitexal and doxorubicin have been successfully administered clinically in numerous cancer types. Together with C6 ceramide, taxol synergistically inhibits cell proliferation and cell migration. To further determine whether taxol affects C6 ceramide entry into ovarian cancer cells, in the present study, the cells were pretreated with taxol for 1 h and then treated with C6-NBD. The results indicated that taxol disrupted the polarized pattern of C6 entry. Notably, doxorubicin, a commonly utilized therapeutic agent, had no such effect (FIG. 12A). The combination of C6-NBD and taxol was observed to induce vesicle formation (FIG. 12B).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating pancreatic cancer comprising the step of: contacting a pancreatic cancer cell with an effective amount of a composition consisting essentially of (a) C6-ceramide; (b) an anti-cancer agent; and (c) a lipid, wherein the lipid consists essentially of two or more of 1,2-dipalmitoyl-sn-glycero-3-galloyl, 1,2-distearoyl-sn-glycero-3-phosphoethanolamine-N-[methoxy(polyethylene glycol)-2000], and 1,2-dioleoyl-sn-glycero-3-phosphocholine, thereby treating pancreatic cancer, wherein the anti-cancer agent is selected from the group consisting of paclitaxel, gemcitabine, oxaliplatin, cisplatin, cetuximab, panitumumab, erlotinib, daunorubicin, doxorubicin, cytosine arabinoside, and suramin.

2. The method of claim 1, wherein the cell is present in a subject in vivo; and the subject is a mammal.

3. The method of claim 2, wherein the subject is a human.

4. The method of claim 1, wherein the cell is comprised within a pancreatic tumor.

5. The method of claim 1, wherein the pancreatic cancer is pancreatic adenocarcinoma.

6. The method of claim 1, wherein the pancreatic cancer cell has an activating KRAS mutation.

7. The method of claim 6, wherein the activating KRAS mutations is a human KRAS polypeptide having a mutation selected from the group consisting of G12C, G12A, G12D, G12R, G12S, G12V, G13C, and G13D.

8. The method of claim 1, wherein the composition consists essentially of (a) C6-ceramide; (b) the anti-cancer agent; and (c) a lipid consisting essentially of 1,2-dipalmitoyl-sn-glycero-3-galloyl and 1,2-dioleoyl-sn-glycero-3-phosphocholine.

9. The method of claim 1, wherein the composition consists essentially of (a) C6-ceramide; (b) the anti-cancer agent; and (c) a lipid consisting essentially of 1,2-distearoyl-sn-glycero-3-phosphoethanolamine-N-[methoxy(polyethylene glycol)-2000] and 1,2-dioleoyl-sn-glycero-3-phosphocholine.

10. The method of claim 1, wherein the weight ratio of (a):(b) is from about 2:1 to about 1:40.

11. The method of claim 1, wherein the anti-cancer agent comprises paclitaxel.

12. The method of claim 1, wherein the anti-cancer agent comprises gemcitabine.

13. The method of claim 1, wherein the anti-cancer agent comprises cetuximab.

14. The method of claim 1, wherein the treatment of cancer is determined by analyzing at least one condition caused by contacting the cell with the composition relative to the state of the condition in the absence of contacting the cell with the composition, wherein the at least one condition is selected from the group consisting of increased apoptosis, decreased mean rate of tumor development (MRTD), decreased mean tumor volume (MTV), decreasing mean tumor size (MTS), increasing mean body weight (MBW), increased mean survival time (MST), increased survival until mortality, pathological complete response, clinical complete remission, clinical partial remission, clinical stable disease, recurrence-free survival, metastasis free survival, and disease free survival.

15. The method of claim 14, wherein the condition is affected synergistically with respect to contacting the cell with the composition relative to the condition affected by contacting the cell with (a) alone, (b) alone, (c) alone, (a) and (b) together, (a) and (c) together, or (b) and (c) together.

16. The method of claim 1, wherein the anti-cancer agent comprises 5-fluorouracil and oxaliplatin.

17. The method of claim 1, wherein the anti-cancer agent comprises 5-fluorouracil, oxaliplatin, and cetuximab.

18. The method of claim 1, wherein the anti-cancer agent comprises cisplatin.

19. The method of claim 1, wherein the anti-cancer agent comprises oxaliplatin.

20. The method of claim 1, wherein the anti-cancer agent comprises doxorubicin.

21. The method of claim 1, wherein the anti-cancer agent is paclitaxel, gemcitabine or cisplatin.

* * * * *

SEQUENCE LISTING

<160> NUMBER OF SEQ ID NOS: 4

<210> SEQ ID NO 1

<211> LENGTH: 570
<212> TYPE: DNA
<213> ORGANISM: Homo sapiens

<400> SEQUENCE: 1

```
atgactgaat ataaacttgt ggtagttgga gctggtggcg taggcaagag tgccttgacg      60
atacagctaa ttcagaatca ttttgtggac gaatatgatc caacaataga ggattcctac     120
aggaagcaag tagtaattga tggagaaacc tgtctcttgg atattctcga cacagcaggt     180
caagaggagt acagtgcaat gagggaccag tacatgagga ctggggaggg ctttctttgt     240
gtatttgcca taataatac taaatcattt gaagatattc accattatag agaacaaatt     300
aaaagagtta aggactctga agatgtacct atggtcctag taggaaataa atgtgatttg     360
ccttctagaa cagtgacac aaaacaggct caggacttag caagaagtta tggaattcct     420
tttattgaaa catcagcaaa gacaagacag agagtggagg atgcttttta tacattggtg     480
agggagatcc gacaatacag attgaaaaaa atcagcaaag aagaaaagac tcctggctgt     540
gtgaaaatta aaaaatgcat tataatgtaa                                      570
```

<210> SEQ ID NO 2
<211> LENGTH: 189
<212> TYPE: PRT
<213> ORGANISM: Homo sapiens

<400> SEQUENCE: 2

```
Met Thr Glu Tyr Lys Leu Val Val Val Gly Ala Gly Gly Val Gly Lys
  1               5                  10                  15

Ser Ala Leu Thr Ile Gln Leu Ile Gln Asn His Phe Val Asp Glu Tyr
             20                  25                  30

Asp Pro Thr Ile Glu Asp Ser Tyr Arg Lys Gln Val Val Ile Asp Gly
         35                  40                  45

Glu Thr Cys Leu Leu Asp Ile Leu Asp Thr Ala Gly Gln Glu Glu Tyr
     50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

<210> SEQ ID NO 3
<211> LENGTH: 567
<212> TYPE: DNA
<213> ORGANISM: Homo sapiens

<400> SEQUENCE: 3

```
atgactgaat ataaacttgt ggtagttgga gctggtggcg taggcaagag tgccttgacg      60
```

```
atacagctaa ttcagaatca ttttgtggac gaatatgatc caacaataga ggattcctac      120
aggaagcaag tagtaattga tggagaaacc tgtctcttgg atattctcga cacagcaggt      180
caagaggagt acagtgcaat gagggaccag tacatgagga ctggggaggg ctttctttgt      240
gtatttgcca taaataatac taaatcattt gaagatattc accattatag agaacaaatt      300
aaaagagtta aggactctga agatgtacct atggtcctag taggaaataa atgtgatttg      360
ccttctagaa cagtagacac aaaacaggct caggacttag caagaagtta tggaattcct      420
tttattgaaa catcagcaaa gacaagacag ggtgttgatg atgccttcta tacattagtt      480
cgagaaattc gaaaacataa agaaaagatg agcaaagatg gtaaaagaa gaaaaagaag      540 tcaaagacaa agtgtgtaat tatgtaa                                         567
```

<210> SEQ ID NO 4
<211> LENGTH: 188
<212> TYPE: PRT
<213> ORGANISM: Homo sapiens

<400> SEQUENCE: 4

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```